US009724348B2

(12) United States Patent
Wu

(10) Patent No.: US 9,724,348 B2

(45) Date of Patent: Aug. 8, 2017

(54) CRYSTALLINE FORMS

(71) Applicant: VM Therapeutics LLC, Fremont, CA (US)

(72) Inventor: Jay Jie-Qiang Wu, Fremont, CA (US)

(73) Assignee: VM Therapeutics LLC, Fremont, CA (US)

( * ) Notice: Subject to any disclaimer, the term of this patent is extended or adjusted under 35 U.S.C. 154(b) by 0 days.

(21) Appl. No.: 14/776,365

(22) PCT Filed: Mar. 14, 2014

(86) PCT No.: PCT/US2014/028093

§ 371 (c)(1),
(2) Date: Sep. 14, 2015

(87) PCT Pub. No.: WO2014/143915

PCT Pub. Date: Sep. 18, 2014

(65) Prior Publication Data

US 2016/0038493 A1 Feb. 11, 2016

Related U.S. Application Data

(60) Provisional application No. 61/800,420, filed on Mar. 15, 2013.

(51) Int. Cl.
*A61K 31/519* (2006.01)
*C07D 471/04* (2006.01)

(52) U.S. Cl.
CPC .......... *A61K 31/519* (2013.01); *C07D 471/04* (2013.01)

(58) Field of Classification Search
CPC ............................ C07D 471/04; A61K 31/519
See application file for complete search history.

(56) References Cited

U.S. PATENT DOCUMENTS

| | | | |
|---|---|---|---|
| 4,342,870 | A | 8/1982 | Kennis et al. |
| 5,112,598 | A | 5/1992 | Biesalski |
| 5,556,611 | A | 9/1996 | Biesalski |
| 5,698,155 | A | 12/1997 | Grosswald et al. |

FOREIGN PATENT DOCUMENTS

| | | | |
|---|---|---|---|
| EP | 0037265 | A1 | 10/1981 |
| WO | WO 2009/108798 | A1 | 9/2009 |
| WO | WO 2014/143915 | A1 | 9/2014 |

OTHER PUBLICATIONS

Ansseau, M. et al., "Pilot study of a specific serotonergic antagonist, pirenperone, in the treatment of anxiety disorders", Acta Psychiatr Belg. (1983), 83(5): 517-24.
Bennett and Xie, "A peripheral mononeuropathy in rat that produces disorders of pain sensation like those seen in man", Pain (1988), 33(1): 87-107.
Bundgaard and Møss, "Prodrugs of peptides. IV: Bioreversible derivatization of the pyroglutamyl group by N-acylation and N-aminomethylation to effect protection against pyroglutamyl aminopeptidase", J Pharm Sci. (1989), 78(2): 122-126.
Kim and Chung., "An experimental model for peripheral neuropathy produced by segmental spinal nerve ligation in the rat", Pain (1992), 50(3): 355-363.
Okada, H. et al., "Synthesis and antitumor activities of prodrugs of benzoylphenylureas", Chem Pharm Bull (1994), 42(1): 57-61.
PCT/US2014/028093, International Search Report and Written Opinion, mailed Aug. 27, 2014.
PCT/US2014/028093, International Preliminary Report on Patentability, dated Sep. 15, 2015.
Blaton, N.M., et al. "3-{2-[4-(4-Fluorobenzoyl) piperidino] ethyl}-2-methyl-4H-pyrido [1, 2-a] pyrimidin-4-one (Pirenperone)." Acta Crystallographica Section C: Crystal Structure Communications (1995); 51.3: 533-535.
Caira, Mino R. "Crystalline polymorphism of organic compounds." Topics in Current Chemistry (1998); 198: 163-208.
European Patent Application No. EP 14764377.9, Extended European Search Report mailed Sep. 16, 2016, 7 pages.
Koval'Chukova, O. V., et al. "Crystal structure and spectral characteristics of 2-methyl-3-chloro-9-hydroxypyrido [1, 2-a] pyrimidin-4-one and bis (2-methyl-3-chloro-9-hydroxypyrido [1, 2-a] pyrimidin-4-onium) perchlorate." Crystallography Reports (2004); 49.5: 792-797.

*Primary Examiner* — Alexander R Pagano
*Assistant Examiner* — Ebenezer O Sackey
(74) *Attorney, Agent, or Firm* — Cooley LLP

(57) ABSTRACT

The present invention relates to novel crystalline polymorphic forms of 3-(2-{4-[(4-fluorophenyl)carbonyl]piperidin-1-yl}ethyl)-2-methyl-4H-pyrido[1,2-α]pyrimidin-4-one. The present invention also includes the methods of making crystalline polymorphic forms thereof and the use thereof for preparing a pharmaceutical composition.

48 Claims, 19 Drawing Sheets

CRYSTALLINE FORMS

CROSS REFERENCE TO RELATED APPLICATIONS

This Application is a National Stage Application, filed pursuant to 35 U.S.C §371, of International Application No. PCT/US2014/028093, filed on Mar. 14, 2014, which claims priority to U.S. Provisional Application No. 61/800,420, filed Mar. 15, 2013, the entire contents of which are hereby incorporated by reference in their entirety for all purposes.

FIELD OF THE INVENTION

The present invention relates to novel crystalline polymorphic forms of 3-(2-{4-[(4-fluorophenyl)carbonyl]piperidin-1-yl}ethyl)-2-methyl-4H-pyrido[1,2-a]pyrimidin-4-one. The present invention also includes the methods of making crystalline polymorphic forms thereof and the use thereof for preparing a pharmaceutical composition.

SUMMARY OF THE INVENTION

A compound, 3-(2-{4-[(4-fluorophenyl)carbonyl]piperidin-1-yl}ethyl)-2-methyl-4H-pyrido[1,2-a]pyrimidin-4-one has the following chemical structure:

Compound 10

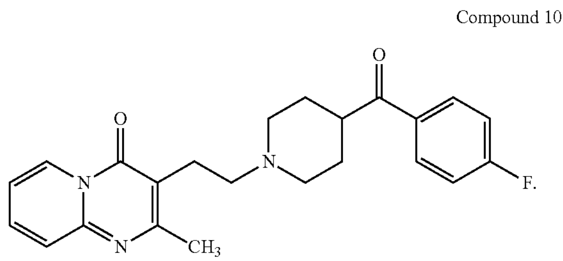 [SMILES: Cc1nc2ccccn2c(=O)c1CCN1CCC(C(=O)c2ccc(F)cc2)CC1]

It was first disclosed in the now-expired U.S. Pat. No. 4,342,870 (claim 5), and intended to be used as potential anti-anxiety drug. However, the early human clinical studies has shown that the compound did not show any dose-related anti-anxiety effects as hoped, but otherwise the compound was safe in human (ref. Ansseau M, Doumont A, Thiry D, Gelders Y. "Pilot study of a specific serotonergic antagonist, pirenperone, in the treatment of anxiety disorders", Acta Psychiatr Belg. 1983 Sep.-Oct.; 83(5):517-24). In the U.S. Pat. No. 4,342,870, there is no crystalline polymorphic form disclosed, nor disclosure of potential uses for management of pain and treatment of other related diseases or disorders.

It was further disclosed in the PCT patent application WO/2009/108798 as "Compound 10 (pirenperone)" to be used for novel T-type calcium ion channel antagonist for management of pain and treatment of other diseases or disorders associated to the T-type calcium ion channels.

Surprisingly, we have found that there are many crystalline polymorphic forms of this compound which may affect the compound's pharmaceutical safety and pharmacology properties.

In one aspect, the current invention presents new, stable polymorph forms, which can be used as pharmaceutical active ingredients. The crystalline polymorphs of compound 10 can be one or more of crystalline polymorph Forms 1, 2, 3, 4, 5, 2', 6, and 7.

In an embodiment, crystalline polymorph Form 1 has x-ray powder diffraction pattern comprising peaks with degrees two-theta positions of about 17.2±0.3, 22.6±0.3, and 27.4±0.3. In another embodiment, the x-ray powder diffraction pattern further comprises peaks with degrees two-theta positions of about 23.3±0.3 and 17.7±0.3. In another embodiment, the x-ray powder diffraction pattern further comprises peaks with degrees two-theta positions of 21.9±0.3 and 20.1±0.3. In still another embodiment, the x-ray powder diffraction pattern comprises five or more, seven or more, ten or more, or all of the peaks with degrees two-theta positions selected from the group consisting of about 4.482, 9.000, 12.248, 13.542, 14.596, 16.137, 17.126, 17.6667, 18.396, 19.419, 20.092, 21.885, 22.551, 23.3092, 26.787, and 27.361. In yet another embodiment, the x-ray powder diffraction pattern is substantially similar to that of FIG. 1. In a further embodiment, crystalline polymorph Form 1 has a Raman spectrum comprising the three or five of most intense peaks of FIG. 2, or a Raman spectrum that is substantially similar to FIG. 2. In an additional embodiment, the crystalline polymorph has a differential scanning calorimitry thermogram exhibiting an endotherm with one or more of an onset of about 124° C., an endotherm with a peak of about 128° C., an exotherm with an onset of about 157° C., and an exotherm with a peak of about 157° C. In a particular embodiment, the differential scanning calorimitry thermogram is substantially similar to FIG. 3.

In further embodiments, a crystalline polymorph can be a crystalline polymorph Form 2 of compound 10. The crystalline polymorph Form 2 can have an x-ray powder diffraction pattern comprising peaks with degrees two-theta positions of about 5.1±0.3, 12.7±0.3, and 22.0±0.3. In other embodiments, the crystalline polymorph Form 2 can have an x-ray powder diffraction pattern further comprising peaks with degrees two-theta positions of about 16.3±0.3 and 15.5±03. In other embodiments, the crystalline polymorph Form 2 can have an x-ray powder diffraction pattern further comprising peaks with degrees two-theta positions of about 18.5±0.3 and 19.6±03. In other embodiments, the crystalline polymorph Form 2 can have an x-ray powder diffraction pattern comprising five or more, seven or more, ten or more, or all of the peaks with degrees two-theta positions selected from the group consisting of about 5.181, 9.338, 10.301, 11.616, 12.883, 15.580, 16.339, 17.321, 18.560, 18.998, 19.702, 22.048, 23.339, 23.740, 24.00, 25.441, 28.460, 29.219, 29.563, and 31.379. In yet another embodiment, the x-ray powder diffraction pattern is substantially similar to that of FIG. 4. In yet other embodiments, the crystalline polymorph Form 2 can have a differential scanning calorimetry thermogram exhibiting one or more of an endotherm with an onset of about 160° C. and an endotherm with a peak of about 163° C. In a particular embodiment, the differential scanning calorimitry thermogram is substantially similar to FIG. 5. In yet another embodiment, the Infrared (IR) spectrum pattern is substantially similar to that of FIG. 17.

In still further embodiments, a crystalline polymorph can be a crystalline polymorph Form 3 of compound 10. The crystalline polymorph Form 3 can have an x-ray powder diffraction pattern comprising peaks with degrees two-theta positions of about 16.0±0.3, 21.7±0.3, and 26.7±0.3. In yet further embodiments, the x-ray powder diffraction pattern can comprise peaks with degrees two-theta positions of about 11.1±0.3 and 20.3±0.3. In still further embodiments, the x-ray powder diffraction pattern can comprise fiver or more, seven or more, ten or more, or all of the peaks at degrees two-theta positions selected from the group consisting of about 11.070, 13.178, 14.801, 16.045, 20.301, 20.800, 21.687, 22.368, 23.048, 23.884, 24.835, 26.660, and 35.667.

In yet another embodiment, the x-ray powder diffraction pattern is substantially similar to that of FIG. 6.

In additional embodiments, a crystalline polymorph can be a crystalline polymorph Form 4 of compound 10. The crystalline polymorph Form 4 can have an x-ray powder diffraction pattern comprising peaks at degrees two-theta positions of about 23.9±0.3, 26.2±0.3, and 27.9±0.3. In other embodiments, the x-ray powder diffraction pattern can comprise peaks at degrees two-theta positions of about 21.4±0.3 and 27.9±0.3. In still other embodiments, the x-ray powder diffraction pattern comprises peaks at five or more, seven or more, ten or more, or all degrees two-theta positions selected from the group consisting of about 10.473, 13.598, 14.502, 15.679, 18.338, 18.955, 19.401, 21.423, 21.861, 22.138, 23.851, 24.511, 25.815, 26.244, 27.043, 27.584, 27.948, 28.547, 29.553, and 31.200. In yet another embodiment, the x-ray powder diffraction pattern is substantially similar to that of FIG. 7.

In some embodiments, the crystalline polymorph is a crystalline polymorph Form 5 of compound 10. The crystalline polymorph Form 5 of compound 10 can comprise peaks with degrees two-theta positions of about 19.8±0.3, 22.3±0.3, and 23.3±0.3. In some additional embodiments, the crystalline polymorph Form 5 of compound 10 can have an x-ray powder diffraction pattern that comprises peaks with degrees two-theta positions of about 15.5±0.3 and 23.9±0.3. In yet additional embodiments, the x-ray powder diffraction pattern of crystalline polymorph Form 5 can comprise five or more, seven or more, ten or more, or all of the peaks with degrees two-theta positions selected from the group consisting of about 5.157, 7.600, 9.823, 10.412, 11.221, 13.456, 14.512, 15.314, 15.739, 16.325, 16.832, 17.354, 17.828, 18.485, 19.367, 20.320, 21.077, 21.708, 22.328, 23.319, 23.905, 25.197, 25.916, 27.770, 28.511, 29.132, 30.399, and 37.203. In yet additional embodiments, the x-ray powder diffraction pattern of crystalline polymorph Form 5 can be substantially similar to FIG. 8. The crystalline polymorph Form 5 can, in some embodiments, have a differential scanning calorimitry thermogram comprising one or more of an exotherm with an onset of about 89° C., an exotherm with a peak of about 96° C., an exotherm with an onset of about 127° C., an exotherm with a peak of about 131° C., an exotherm with an onset of about 153° C., and a thermogram that is substantially similar to FIG. 10.

In other embodiments, the crystalline polymorph can be a crystalline polymorph Form 2' of compound 10. The crystalline polymorph Form 2' of compound 10 can comprise peaks with degrees two-theta positions of about 8.8±0.3, 19.5±0.3, and 30.8±0.3. In some additional embodiments, the crystalline polymorph Form 2' of compound 10 can have an x-ray powder diffraction pattern that further comprises peaks with degrees two-theta positions of about 18.8±0.3, 23.2±0.3, and 23.8±0.3. In yet other embodiments, the crystalline polymorph can have an x-ray powder diffraction pattern comprising three or more, five or more, seven or more, ten or more, or all of the peaks at positions degree two-theta selected from the group consisting of about 8.8±0.3, 12.5±0.3, 12.8±0.3, 16.2±0.3, 18.4±0.3, 18.8±0.3, 19.5±0.3, 23.2±0.3, 23.8±0.3, 25.4±0.3, 29.6±0.3 and 30.8±0.3. In still other embodiments, the x-ray powder diffraction pattern can be substantially similar to that of FIG. 11.

In some embodiments, a method of preparing any of the foregoing crystalline polymorphs can include dissolving compound 10 in a solvent that comprises at least one organic solvent at a temperature above ambient temperature and evaporating at least part of the organic solvent to induce precipitation of the crystalline polymorph. In other embodiments, a method of preparing any of the foregoing crystalline polymorphs can include suspending or dissolving compound 10 in a hot solvent to form a suspension or solution; and rapidly cooling the suspension or solution to below the freezing point of water to form a precipitate of the crystalline polymorph. In still other embodiments, a method of preparing any of the foregoing crystalline polymorphs can include dissolving compound 10 in a solvent comprising an organic solvent to form a solution; and adding an anti-solvent to the solution to precipitate the crystalline polymorph. In other embodiments, a method of preparing any of the foregoing crystalline polymorphs can include dissolving compound 10 in a solvent at or above ambient temperature; and recrystallizing the compound 10 to precipitate the crystalline polymorph. In another embodiment, a method of preparing any of the foregoing crystalline polymorphs can include spending compound 10 in a solvent comprising an organic solvent to form a slurry; and iteratively heating and cooling the slurry to precipitate the crystalline polymorph. In particular embodiments, iteratively heating and cooling the slurry can comprise heating the slurry to a temperature above ambient temperature one or more times, and cooling the slurry to ambient temperature or lower one or more times.

In any of the foregoing methods of making embodiments, the organic solvent can comprise one or more of tetrahydrofuran, methanol, acetone, toluene, dichloromethane, 1,4-dioxane, tetrahydrofuran and water mixture, ethanol and water mixture, ethyl acetate, acetonitrile, diethyl ether, and dimethylformamide, and the anti-solvent, if used, can comprise one or more of water, pentane, and methyl tert-butyl ether. In any of the foregoing methods of making embodiments, the acid, if used, can comprise an organic acid such as acetic acid. In any of the foregoing methods of making embodiments, the temperature above ambient temperature can be about 40° C.

In a particular embodiment, a process of preparing crystalline polymorph 2' can include heating a crystalline polymorph of compound 10. In specific embodiments, the crystalline polymorph of compound 10 is one or more of crystalline polymorphs 1, 2, 3, 4, and 5. In some embodiments, the heating comprises removing at least some water from the crystalline polymorph.

In another embodiment, one or more of the foregoing crystalline polymorphs is in a combination with one or more pharmaceutically acceptable excipients. In still another embodiment, a solid or semi-solid dosage form comprises any of the foregoing crystalline polymorphs or the foregoing combination.

In yet another embodiment, a method of preparing a medicament comprises combining one or more of the foregoing crystalline polymorphs with one or more pharmaceutically acceptable excipients. In still another embodiment, the medicament is useful for treating a disease, disorder, or condition associated with T-type calcium ion channels. In other embodiments, the medicament is useful for treating one or more of acute pain, chronic pain, neuropathic pain, inflammatory pain, radicular pain, sciatica, back pain, head pain, neck pain, severe or intractable pain, post-surgical pain, visceral pain, cancer pain, osteoarthritis pain, peripheral neuropathy, nociceptive pain, breakthrough pain, migraine, angina, vascular disease, arteriosclerosis, sleep disorders, metabolic disorders, gastrointestinal disease, prostate tumor or cancer, schizophrenia, drug dependence, tinnitus, dementia, asthma, cluster headaches, trigeminal neuralgia, herpetic neuralgia, general neuralgias, epilepsy, neurodegenerative disorders, arthritis, anxiety, depression, myotonia, arrythmia, movement disorders, neuroendocrine disorders, ataxia, multiple sclerosis, irritable bowel syndrome, incontinence, postherpetic neuralgia, diabetic neuropathy, or cancer, contraception, nervous system injury, seizure, convulsion, Huntington's chorea, Alzheimer' disease, autoimmune disease, tremor, Parkinson's diseases, Amyotrophic Lateral Sclerosis (ALS), retinopathy, neoplasm, inflammation, cranial neuropathy, type 1 or type 2 diabetes, hyperaldosteronemia, preterm labor, urinary incontinence, and brain aging.

A method of treating a subject can, in some embodiments, include administering to the subject one or more of the foregoing crystalline polymorphs, combinations, medicaments, or dosage forms. In further embodiments, the method comprises treating the subject for one or more of the aforementioned conditions, diseases, or disorders.

In another aspect, the invention also provides the most stable crystalline polymorphic form for pharmaceutical uses.

DETAILED DESCRIPTION OF THE INVENTION

Figure 1:
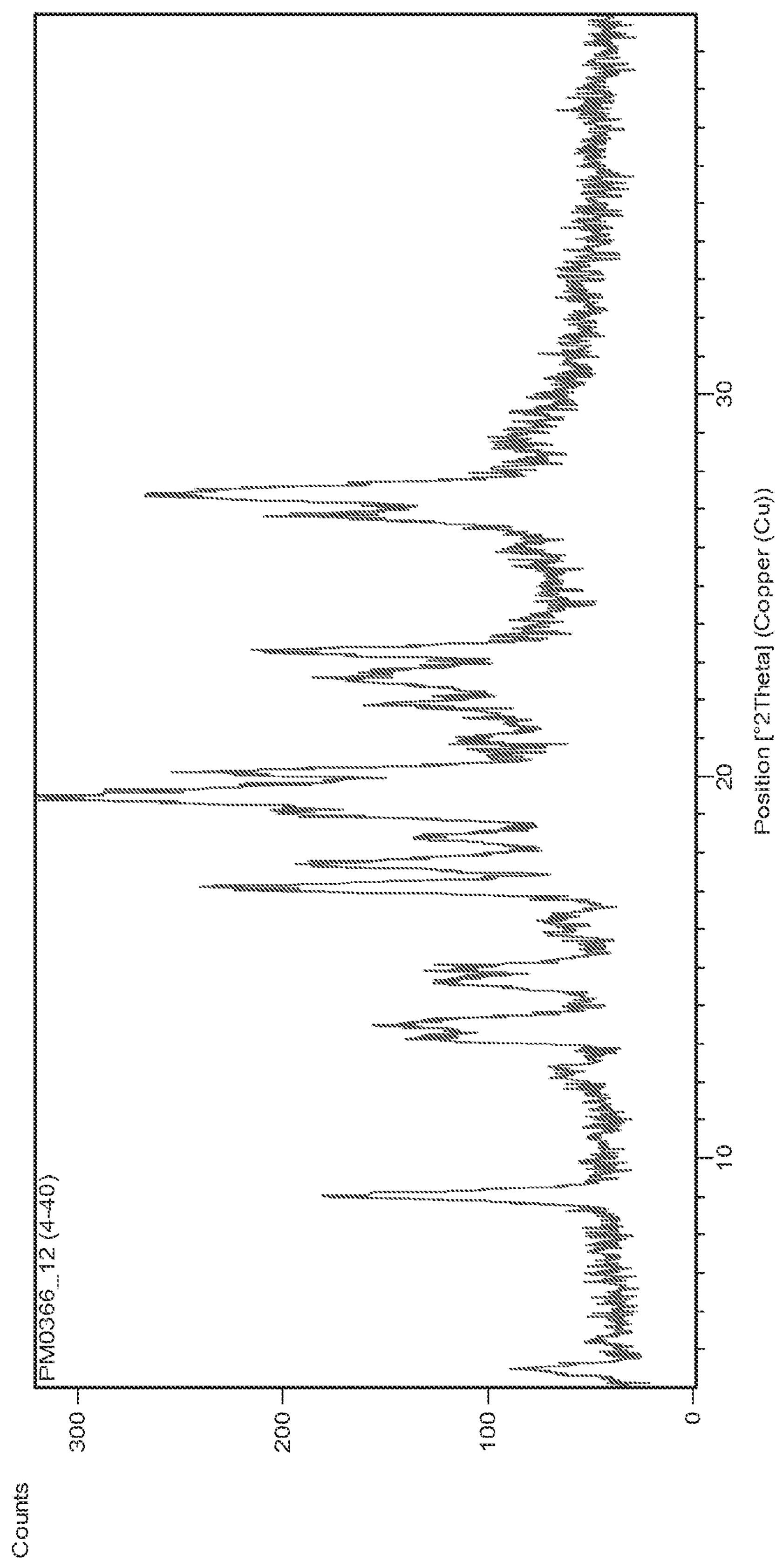
FIG. 1 is an X-ray powder diffraction (XRPD) spectrum of the crystalline polymorph Form 1 of Compound 10.

It should be understood that singular prepositions such as "a," "an," and "the," are often used for convenience, however, all instances of the singular are intended to encompass the plural unless otherwise indicated either explicitly or from context. Further, it should be understood that all references, including journal articles, books, patents, technical documents, and the like, mentioned in this disclosure are hereby incorporated by reference in their entirety and for all purposes.

Furthermore, all numerical data points should be understood to be modified by the term "about" as will be elaborated upon in the disclosure.

Definitions

The term "physiologically functional derivative(s)" as used herein refers to any physiologically tolerated derivative of a compound of the present invention, for example, an ester or prodrug, which, upon administration to a mammal, e.g., a human, are transformed directly or indirectly to Compound I, or an active metabolite thereof. Physiologically functional derivatives include prodrugs of the compounds of the present invention. Examples of prodrug are described in H. Okada et al., Chem. Pharm. Bull. 1994, 42, 57-61. Such prodrugs can be metabolized in vivo to a compound of the invention. These prodrugs may themselves be active or not.

Compounds of the present invention also include isotopically labeled compounds where one or more atoms have an atomic mass different from the atomic mass conventionally found in nature. Examples of isotopes that may be incorporated into the compounds include, but are not limited to, 2H, 3H, 13C, 14C, 15N, 17O, 18O, etc. Compounds may exist in unsolvated forms as well as solvated forms, including hydrated forms and as N oxides. In general, the salt, hydrated, solvated, and N oxide forms are within the scope of the present invention. Certain compounds of the present invention may exist in multiple crystalline forms or an amorphous form. In general, all physical forms are equivalent for the uses contemplated by the present invention and are intended to be within the scope of the present invention.

"Patient" or "subject" includes, but is not limited to, animals such as, for example, mammals. Preferably, the patient is a human.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Solvate" means a compound formed by solvation (the combination of solvent molecules with molecules or ions of the solute, i.e., a compound of the present invention), or an aggregate that consists of a solute ion or molecule (the compound of the present invention) with one or more solvent molecules.

"Pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Prodrug or softdrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug or softdrug is an ester or an ether form of a pharmaceutically active compound. Several prodrugs have been prepared and disclosed for a variety of pharmaceuticals. See, for example, Bundgaard, H. and Moss, J., J. Pharm. Sci. 78: 122-126 (1989). Thus, one of ordinary skill in the art knows how to prepare these precursors, prodrugs or softdrugs with commonly employed techniques of organic synthesis.

"Treating", "treat" or "treatment" of any disease or disorder refers, in some embodiments, to ameliorating or preventing the disease or disorder (i.e., arresting, preventing, holding or reducing the development of the disease or at least one of the clinical symptoms thereof). In other embodiments "treating", "treat" or "treatment" refers to ameliorating at least one physical parameter, which may not be discernible by the patient. In yet other embodiments, "treating", "treat" or "treatment" refers to inhibiting, or holding or preventing the progress of, the disease or disorder, either physically, (e.g., stabilization of a discernible symptom), physiologically, (e.g., stabilization of a physical parameter) or both. In yet other embodiments, "treating", "treat" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Vehicle" refers to a diluent, adjuvant, excipient or carrier with which a compound is administered.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

The phrases "an effective amount" and "an amount sufficient to" refer to amounts of a biologically active agent that produce an intended biological activity.

The term "co-administer" or "co-administering" when used in reference to the administration of a compound of current invention and other agents indicates that other agent(s) are administered in a coordinated fashion so that there is at least some chronological overlap in their physiological activity on the subject. Thus, a compound of current invention can be administered simultaneously and/or sequentially with another agent. In sequential administration, there may even be some substantial delay (e.g., minutes or even hours or days) before administration of the second agent as long as the first administered agent is exerting some physiological effect on the organism when the second administered agent is administered or becomes active in the subject.

The term "reducing pain," as used herein, refers to decreasing the level of pain a subject perceives relative to the level of pain the subject would have perceived were it not for the intervention. Where the subject is a person, the level of pain the person perceives can be assessed by asking him or her to describe the pain or compare it to other painful experiences. Alternatively, pain levels can be determined by measuring the subject's physical responses to the pain, such as the release of stress-related factors or the activity of pain-transducing nerves in the peripheral nervous system or the CNS. One can also determine pain levels by measuring the amount of a well-characterized analgesic required for a person to report that no pain is present or for a subject to stop exhibiting symptoms of pain. A reduction in pain can also be measured as an increase in the threshold at which a subject experiences a given stimulus as painful. In certain embodiments, a reduction in pain is achieved by decreasing "hyperalgesia," the heightened sensitivity to a noxious stimulus, and such inhibition can occur without impairing "nociception," the subject's normal sensitivity to a "noxious" stimulus.

As used with reference to pain reduction, "a subject in need thereof" refers to an animal or person, preferably a person, expected to experience pain in the near future. Such animal or person may have an ongoing condition that is causing pain currently and is likely to continue to cause pain. Alternatively, the animal or person has been, is, or will be enduring a procedure or event that usually has painful consequences. Chronic painful conditions such as diabetic neuropathic hyperalgesia and collagen vascular diseases are examples of the first type; dental work, particularly that accompanied by inflammation or nerve damage, and toxin exposure (including exposure to chemotherapeutic agents) are examples of the latter type.

"Inflammatory pain" refers to pain arising from inflammation. Inflammatory pain often manifests as increased sensitivity to mechanical stimuli (mechanical hyperalgesia or tenderness). For examples, inflammatory pain is due to a condition selected from the group consisting of: burn, sunburn, arthritis, colitis, carditis, dermatitis, myositis, neuritis, mucositis, urethritis, cystitis, gastritis, pneumonitis, and collagen vascular disease.

"Neuropathic pain" refers to pain arising from conditions or events that result in nerve damage. "Neuropathy" refers to a disease process resulting in damage to nerves. "Causalgia" denotes a state of chronic pain following nerve injury. "Allodynia" refers to a condition in which a person experiences pain in response to a normally nonpainful stimulus, such as a gentle touch. For examples, neuropathic pain is due to a condition selected from the group consisting of: causalgia, diabetes, collagen vascular disease, trigeminal neuralgia, spinal cord injury, brain stem injury, thalamic pain syndrome, complex regional pain syndrome type I/reflex sympathetic dystrophy, Fabry's syndrome, small fiber neuropathy, cancer, cancer chemotherapy, chronic alcoholism, stroke, abscess, demyelinating disease, viral infection, antiviral therapy, AIDS, and AIDS therapy. Neuropathic pain is due to an agent selected from the group consisting of: trauma, surgery, amputation, toxin, and chemotherapy.

As used herein, the term "generalized pain disorder" refers to a group of idiopathic pain syndromes (e.g., fibromyalgia, irritable bowel syndrome, and temporomandibular disorders), for which the pathogenic mechanism is currently unknown, characterized by diffuse or generalized pain, and for which a diagnosis of inflammation or neuropathy as the direct cause of pain is excluded.

An "analgesic agent" refers to a molecule or combination of molecules that causes a reduction in pain.

The difference between "acute" and "chronic" pain is one of timing: acute pain is experienced soon (e.g., generally within about 48 hours, more typically within about 24 hours, and most typically within about 12 hours) after the occurrence of the event (such as inflammation or nerve injury) that led to such pain. By contrast, there is a significant time lag between the experience of chronic pain and the occurrence of the event that led to such pain. Such time lag is generally at least about 48 hours after such event, more typically at least about 96 hours after such event, and most typically at least about one week after such event.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert Ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The term "cancer" refers to or describes the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, hepatocellular carcinoma, malignant hepatoma, colorectal cancer, endometrial cancer, kidney cancer, prostate cancer, thyroid cancer, neuroblastoma, pancreatic cancer, glioblastoma multiforme, cervical cancer, stomach cancer, bladder cancer, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

It is to be understood that this invention is not limited to particular methods, reagents, compounds, compositions, or biological systems, which can, of course, vary. It is also to be understood that the terminology used herein is for the purpose of describing particular aspects only, and is not intended to be limiting. As used in this specification and the appended claims, the singular forms "a", "an", and "the" include plural referents unless the content clearly dictates otherwise. Thus, for example, reference to "a compound" includes a combination of two or more compounds or molecules, and the like.

Compound 10, 3-(2-{4-[(4-fluorophenyl)carbonyl]piperidin-1-yl)ethyl)-2-methyl-4H-pyrido[1,2-a]pyrimidin-4-one has following chemical structure:

Compound 10

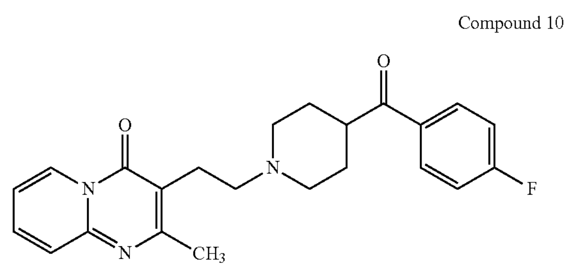 [SMILES: Cc1nc2ccccn2c(=O)c1CCN1CCC(C(=O)c2ccc(F)cc2)CC1]

The present invention includes novel polymorphic forms of this compound. Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

In one embodiment, the crystalline forms are characterized by the interlattice plane intervals determined by a X-ray powder diffraction pattern. The spectrum of XRD is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. In one embodiment, the intensity of about 81% to 100% is very strong; the intensity of about 61% to 80% is strong; the intensity of about 41% to 60% is medium; the intensity of about 21% to 40% is weak; and the intensity of about 1% to 20% is very weak. The characteristic peaks of a given XRD can be selected according to the peak locations and their relative intensity to conveniently distinguish this crystalline structure from others.

Those skilled in the art recognize that the measurements of the XRD peak locations and/or intensity for a given crystalline form of the same compound will vary within a margin of error. The values of degree 2θ allow appropriate error margins. Typically, the error margins are represented by "±". For example, the degree 2θ of about "17.1±0.3" denotes a range from about 17.1±0.3, i.e., about 17.4, to about 17.1−0.3, i.e., about 16.8. Depending on the sample preparation techniques, the calibration techniques applied to the instruments, human operational variation, and etc, those skilled in the art recognize that the appropriate error of margins for a XRD can be ±0.5; ±0.4; ±0.3; ±0.2; ±0.1; ±0.05; or less.

The term "substantially similar" as used herein means an analytical spectrum, such as XRD pattern, $^1$H-NMR spectrum, FT-IR spectrum, Raman spectrum, TGA thermogram, etc., which resembles the reference spectrum to a great degree in both the peak locations and their intensity.

In one aspect, the present invention presents a novel polymorphic crystalline form designated as Form 1 of Compound 10. Form 1 can be characterized by unique strong x-ray powder diffraction (XRPD) peaks at about 17.1±0.3, 19.4±0.3, 22.6±0.3, and 27.4±0.3 degree two-theta.

In one aspect, Form 1 can be further characterized by unique strong x-ray powder diffraction (XRPD) peaks at about 17.7±0.3, 20.1±0.3, and 23.3±0.3 degree two-theta.

In another aspect, the present invention presents a novel polymorphic crystalline form designated as Form 1 of Compound 10. Form 1 can be further characterized by unique strong x-ray powder diffraction (XRPD) peaks at about 4.5±0.3, 9.0±0.3, 12.2±0.3, 13.5±0.3, 14.6±0.3, 16.1±0.3, 17.1±0.3, 17.6±0.3, 18.4±0.3, 19.4±0.3, 20.1±0.3, 21.9±0.3, 22.6±0.3, 23.3±0.3, 26.7±0.3, and 27.4±0.3 degree two-theta.

Form 1 can be prepared by recrystallization of an amorphous or mixed crystal form of compound 10. Fast evaporation (e.g., at elevated temperature) or room temperature evaporation of the solvent can induce crystallization.

Form 1 can be prepared by a slurry process, where a slurry is temperature-cycled between ambient and about 40° C. for about 48 hours. This can form a solutions for crash cooling after filtering the heated supernatant from the slurries, filtering through a disposable syringe filter and transferring to the freezer at about −26° C. When the API is soluble, supersaturated solutions can be prepared by heating 50 mg/200 mL, and filtering into a new vial which was transferred to the freezer at −26° C.

Antisolvent addition can be used to form Form 1, such as reverse addition of antisolvent. The antisolvent additions were carried out by heating 50 mg compound in 300 mL primary solvent, then the resulting supersaturated suspension was filtered in about 100 ml aliquots into antisolvent (0.5 mL) at ambient temperature. When solid was precipitated, excess liquid was decanted off and the solid products were dried under vacuum.

In another aspect of the present invention, it is a process for preparing Form 1 of Compound 10. Form 1 can be produced from fast evaporation of organic solvents, such as methanol, acetone, toluene, dichloromethane, 1,4-dioxane, THF/water (7:3) or ethanol and water mixture; or by slurry from acetone, toluene and DCE.

The DSC thermogram of Form 1 can be characterized by solid-solid transition to Form 1 detected in a small exotherm at about 124-127° C., followed by a melting endotherm at about 156-160° C.

In one aspect, the invention presents a novel polymorphic crystalline form designated as Form 2 of Compound 10. Form 2 can be characterized by having x-ray powder diffraction characteristic peak positions of about 5.1±0.3, 9.4±0.3, 12.7±0.4, 15.5±0.3, 16.3±0.3, 18.5±0.3, 19.0±0.3, 19.6±0.3, 22.0±0.3, 23.3±0.3, 23.8±0.3, 25.4±0.3, 29.2±0.3, and 29.6±0.3 degree 2-theta.

In another aspect, the invention presents a novel crystalline polymorph Form 2 of Compound 10, which can have x-ray powder diffraction further characteristic peak positions of about 5.1±0.3, 9.4±0.3, 10.2±0.3, 12.7±0.4, 15.5±0.3, 16.3±0.3, 17.4±0.3, 17.8±0.3, 18.5±0.3, 19.010.3, 19.6±0.3, 20.6±0.3, 22.0±0.3, 23.3±0.3, 23.8±0.3, 25.4±0.3, 28.5±0.3, 29.2±0.3, 29.6±0.3, 31.2±0.3, 33.4±0.3, and 36.3±0.3 degree 2-theta.

Figure 17:
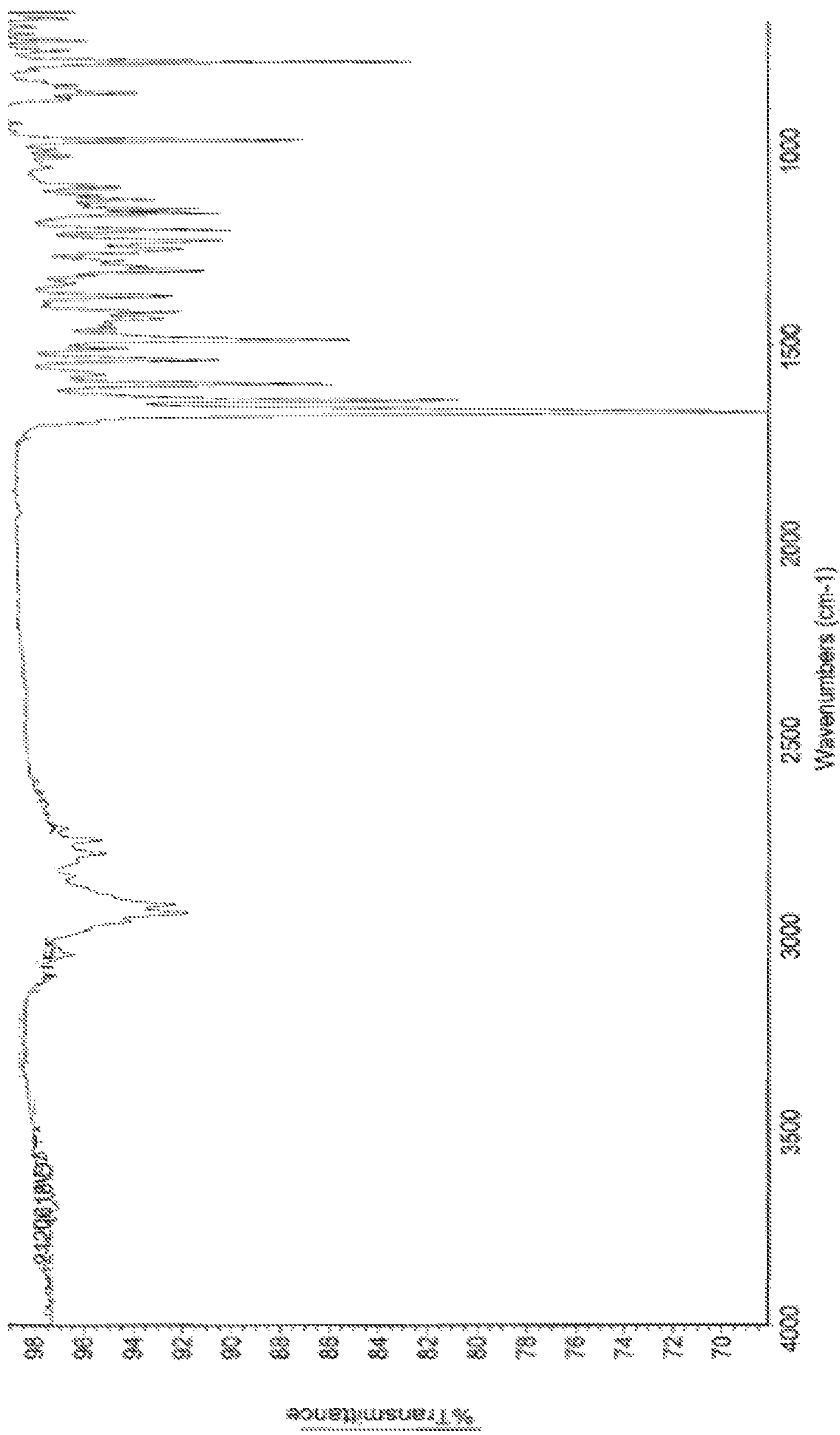
FIG. 17 is an Infrared (IR) spectrum of the crystalline polymorph Form 2 of Compound 10.

In another aspect, the invention provides a novel crystalline polymorph Form 2 of Compound 10, which comprises at least two or more, or three or more, or four or more of the most intense peaks in the Infrared spectrum of FIG. 17. In another embodiment, the invention provides a novel crystalline polymorph Form 2 of Compound 10 having Infrared spectrum substantially similar to that of FIG. 17.

In another aspect of the present invention is a process for preparing Form 2 of Compound 10. Form 2 can be obtained by using a variety of different methods, including recrystallization from: IPA, ethyl acetate, acetonitrile, DMF. Another method is the slurry method discussed in detail above. The solvent can be one or more of ethanol, IPA, ethyl acetate, THF, ACN, 1,4-dioxane, DMF, MTBE, THF/water (7/3), ethanol/water (9/1). Another method is dissolving in a solvent followed by rapid cooling, for example, to lower than the freezing temperature of water such as −26° C. The solvent can be one or more of methanol, IPA, THF, DCE, 1,4-dioxane, DMF, ethanol/water mixtures (e.g. at a 9/1 ratio). Another method is the antisolvent method discussed above. Combinations of solvent/antisolvent that can be used include ethanol/water, ethanol/pentane, MEK/petane, MEK/MTBE, ACN/water, DMF/pentane, IPA/water.

The DSC of Form 2 has a single endotherm at about 160° C. Competitive slurries in IPA, IPA and water, and acetone at ambient temperature and about 40° C., all results in complete conversion to Form 2. Therefore, Form 2 is the most thermodynamically stable form.

In one aspect, the invention presents a novel polymorphic crystalline form designated as Form 3 of Compound 10. Form 3 can be characterized by XRPD peaks at about 16.0±0.3, 20.3±0.3, 21.7±0.3, and 26.7±0.3 degree two-theta.

In another aspect, the invention presents a novel crystalline polymorph Form 3, which can have further characteristic XRPD peak positions at about 8.7±0.3, 11.1±0.3, 13.2±0.3, 14.8±0.3, 15.2±0.3, 16.0±0.3, 17.3±0.3, 19.0±0.3, 19.6±0.3, 20.3±0.3, 20.8±0.3, 21.7±0.3, 22.4±0.3, 23.9±0.3, 24.8±0.3, 25.4±0.3, 26.7±0.3, 28.8±0.3, 30.6±0.3, 30.6±0.3, 31.3±0.3, 32.4±0.3, 32.7±0.3, 33.8±0.3, 35.7±0.3, and 38.8±0.3 degree two-theta.

In another aspect of the present invention is a method of preparing Form 3 of Compound 10 by dissolving Compound 10 in hot solvent, such as THF, and followed by quickly evaporating at least a portion of the solvent to obtain the precipitation of Form 3.

In one aspect, the invention presents a novel polymorphic crystalline form designated as Form 4 of Compound 10. Form 4 can be characterized by XRPD peaks at about 10.5±0.3, 13.6±0.3, 14.5±0.3, 18.3±0.3, 19.0±0.3, 21.4±0.3, 21.8±0.3, 22.1±0.3, 23.9±0.3, 24.5±0.3, 25.8±0.3, 26.3±0.3, 27.0±0.3, 27.6±0.3 and 27.9±0.3 degree two-theta.

In another aspect of the present invention is a method of preparing Form 4 of Compound 10 by dissolving Compound 10 in an organic solvent comprising an acid, such as an organic acid and particularly hot acetic acid, followed by quickly evaporation of the acid or addition of an antisolvent.

In one aspect, the invention presents al polymorphic crystalline form designated as Form 5 of Compound 10. Form 5 can be characterized by XRPD peaks at about 9.8±0.3, 10.4±0.3, 14.5±0.3, 15.3±0.3, 16.8±0.3, 17.4±0.3, 18.5±0.3, 19.9±0.3, 20.6±0.3, 21.1±0.3, 23.3±0.3, 23.9±0.3, 25.2±0.3, 28.5±0.3 and 29.1±0.3 degree two-theta.

In another aspect of the present invention is a method of preparing Form 5 of Compound 10 by mixing Compound 10 with acetic acid to form a slurry, followed by temperature cycling as discussed above to precipitate Form 5.

In one aspect, the invention presents a novel polymorphic crystalline form designated as Form 2' of Compound 10. Form 2' can be characterized by XRPD peaks at about 8.8±0.3, 12.5±0.3, 12.8±0.3, 16.2±0.3, 18.4±0.3, 18.8±0.3, 19.5±0.3, 22.0±0.3, 23.2±0.3, 23.8±0.3, 25.4±0.3, 29.6±0.3 and 30.8±0.3 degree two-theta.

Form 5 which has a similar X-ray pattern to Form 2', can convert to a Form 2' on drying, for example, at 80° C., or during a DSC experiment. This result suggests that Form 5 can be a channel or variable hydrate. Also, Form 5 can be possibly isostructural with Form 2 or Form 2', or the differences between these forms may relate to the presence or absence of a particular amount of surface water.

In another aspect, the invention presents a novel crystalline polymorph Form 6 of Compound 10, which can have x-ray powder diffraction further characteristic peak positions of about 4.94310.3, 10.108±0.3, 12.473±0.3, 12.736±0.3, 15.294±0.3, 16.131±0.3, 18.259±0.3, 18.811±0.3, 19.450±0.3, 20.500±0.3, 21.778±0.3, 23.104±0.3, 23.739±0.3, 25.279±0.3, 29.016±0.3, and 29.487±0.3 degree 2-theta.

In another aspect of the present invention is a process for preparing Form 2 of Compound 10. Form 6 can be obtained by using a variety of different methods, including recrystallization from: IPA, ethyl acetate, acetonitrile, DMF. Another method is the slurry method discussed in detail above. The solvent can be one or more of ethanol, IPA, ethyl acetate, THF, ACN, 1,4-dioxane, DMF, MTBE, THF/water (7/3), ethanol/water (9/1). Another method is dissolving in a solvent followed by rapid cooling, for example, to lower than the freezing temperature of water such as −26° C. The solvent can be one or more of methanol, IPA, THF, DCE, 1,4-dioxane, DMF, ethanol/water mixtures (e.g., at a 9/1 ratio). Another method is the antisolvent method discussed above. Combinations of solvent/antisolvent that can be used include ethanol/water, ethanol/pentane, MEK/petane, MEK/MTBE, ACN/water, DMF/pentane, IPA/water.

In another aspect, the invention presents a novel crystalline polymorph Form 7 of Compound 10, which can have x-ray powder diffraction further characteristic peak positions of about 5.355±0.3, 9.441±0.3, 12.880±0.3, 15.678±0.3, 16.421±0.3, 17.441±0.3, 17.990±0.3, 18.659±0.3, 19.100±0.3, 19.781±0.3, 22.081±0.3, 23.401±0.3, 23.982±0.3, 25.580±0.3, 28.461±0.3, 19.321±0.3, 29.857±0.3, 31.101±0.3, 31.438±0.3, 33.401±0.3, and 36.280±0.3 degree 2-theta.

In another aspect, amorphous form of Compound 10 is also characterized. It can be made by dissolving compound 10 in acetonitrile followed by cooling or addition of antisolvent.

The following examples illustrate methods of preparing crystalline forms carried out by way of examples. The methods presented in examples are intended solely as an illustration, without restricting the invention to its contents.

EXAMPLES

Synthesis of Compound 10

Isopropanol (20 mL), 3-(2-chloroethyl)-2methyl-4H-pyrido[1,2-a]pyrimidin-4-one (2.23, 1 eq), (4-fluorophenyl)(piperidin-4-yl)methanone hydrochloride (2.43 g, 1 eq), sodium carbonate (3.18, 3 eq) and sodium iodide (50 mg) were added to 100 mL 3-neck round bottom flask and stirred with mechanic stirrer. The reaction mixture was heated to 80° C. and allowed reflux for 18 hours. The mixture was filtered hot with rinse of hot isopropanol. Then precipitate from filtrate was collected. The crude product was then recrystallized from hot isopropanol to give material with more than 99% (HPLC) purity and about 60% overall yield. $^{1}$H-NMR (400 MHz, DMSO-d6), ppm (δ): 8.88 (1H, d), 8.08 (2H, t), 8.06 (1H, d), 7.57 (1H, d), 7.38 (2H, t), 7.31 (1H, d), 3.40 (1H, m), 3.01 (2H, m), 2.79 (2H, m), 2.47 (2H, m), 2.17 (2H, m), 1.77 (2H, m), 1.40 (2H, m). Mass spectrum gives [M+1]=394.2.

Preparation of Form 1 of Compound 10

Figure 2:
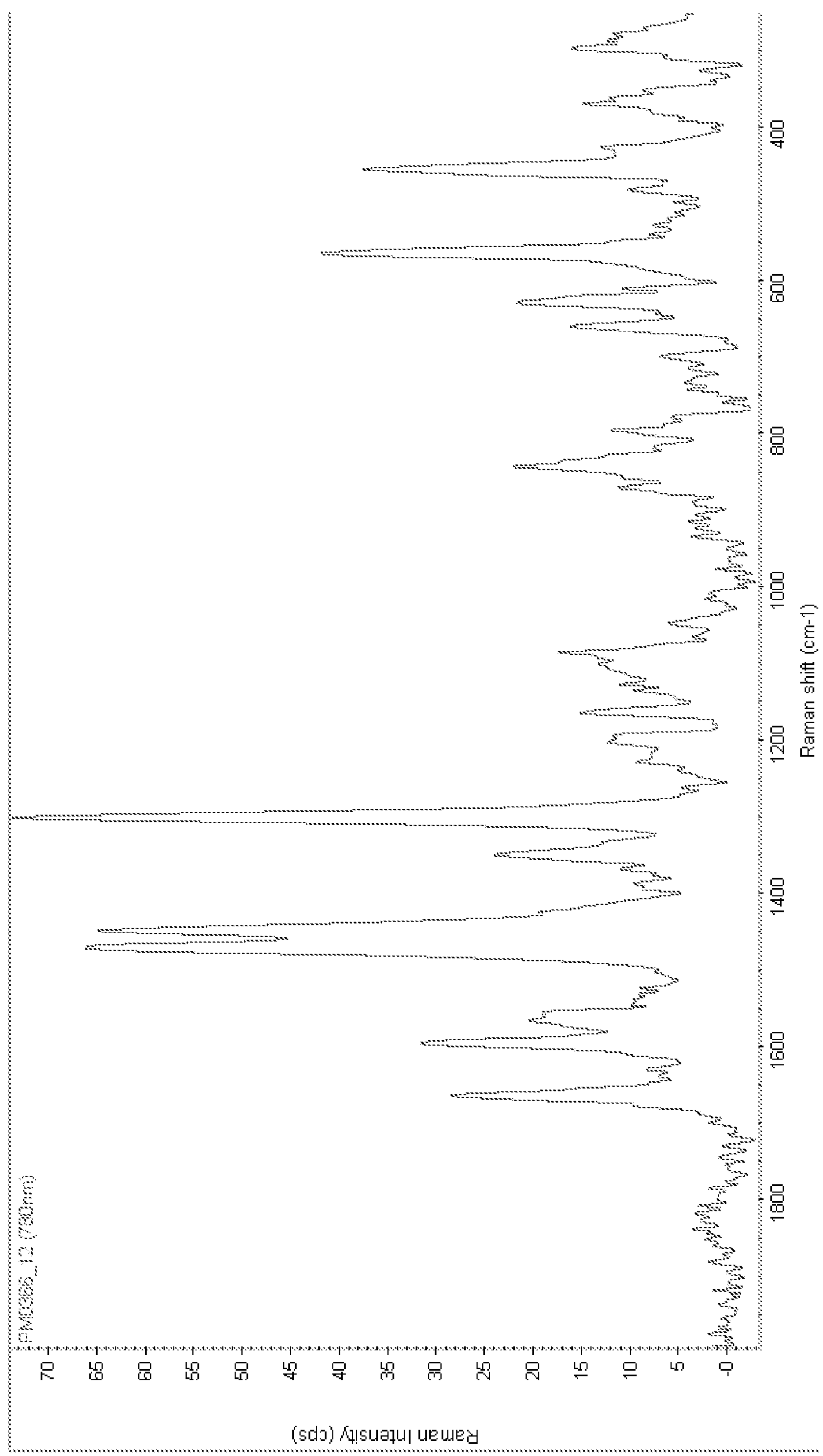
FIG. 2 is a Raman spectrum of the crystalline polymorph Form 1 of Compound 10.
Figure 3:
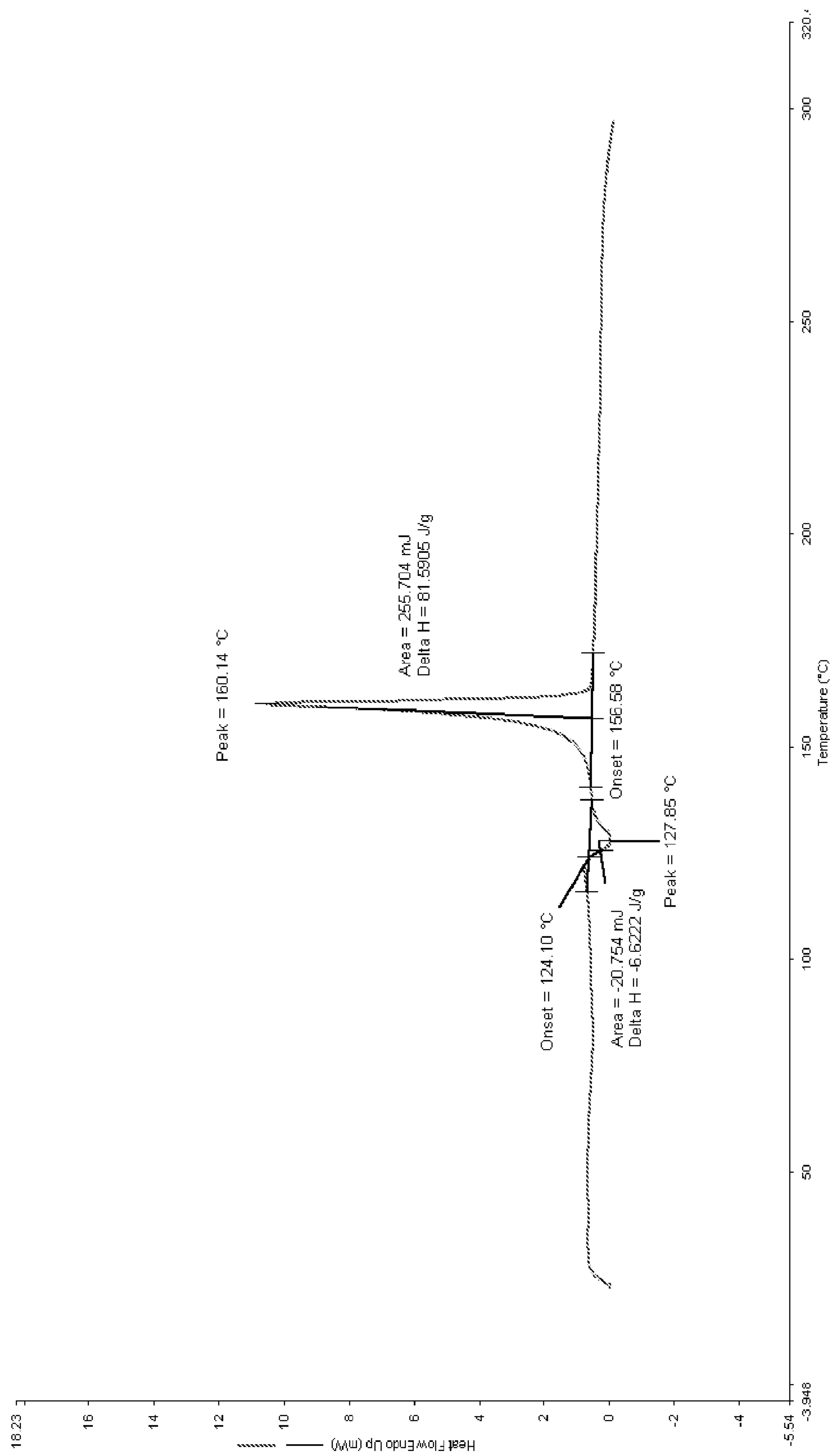
FIG. 3 is a Differential Scanning Calorimetry (DSC) thermogram of Form 1 of Compound 10.

Compound 10 (50 g) was dissolved in hot mixture of ethanol and diethyl ether. The solid was filtered and dried under reduce pressure room temperature. The final API has about 99% (HPLC) purity. The polymorphic Form 1 was confirmed by XRPD (FIG. 1 and Table below), Raman (FIG. 2) and DSC (FIG. 3) spectra.

Form 1

| No. | Pos. [°2Th.] | Rel. Int. [%] |
|---|---|---|
| 1 | 4.4817 | 18.27 |
| 2 | 8.9988 | 30.09 |
| 3 | 12.2481 | 16.11 |
| 4 | 13.542 | 36.85 |
| 5 | 14.5962 | 28.66 |
| 6 | 16.1366 | 9.75 |
| 7 | 17.126 | 92.47 |
| 8 | 17.6663 | 59.04 |
| 9 | 18.3964 | 29.43 |
| 10 | 19.4191 | 100 |
| 11 | 20.092 | 58.09 |
| 12 | 21.885 | 45.93 |
| 13 | 22.5513 | 70.82 |
| 14 | 23.3092 | 65.08 |
| 15 | 26.7865 | 44.05 |
| 16 | 27.3606 | 82.33 |

Preparation of Form 2 of Compound 10

Figure 4:
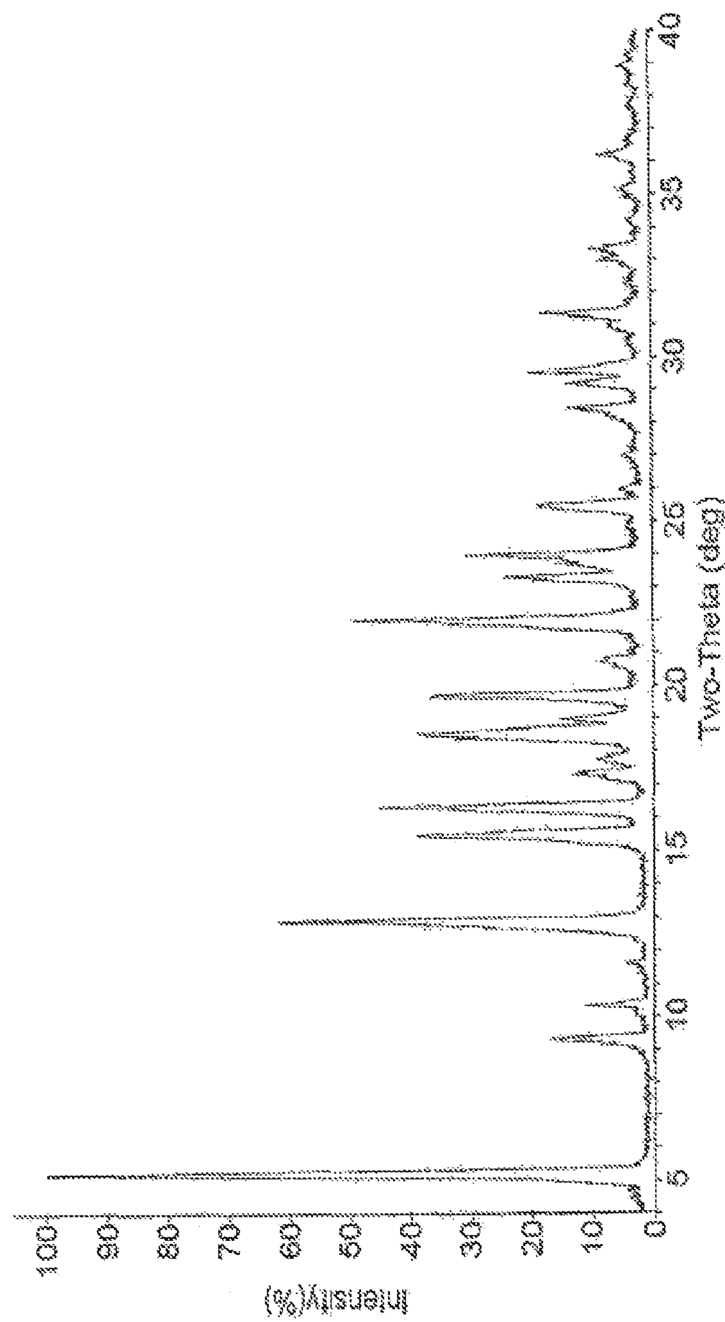
FIG. 4 is an X-ray powder diffraction (XRPD) spectum of the crystalline polymorph Form 2 of Compound 10.
Figure 5:
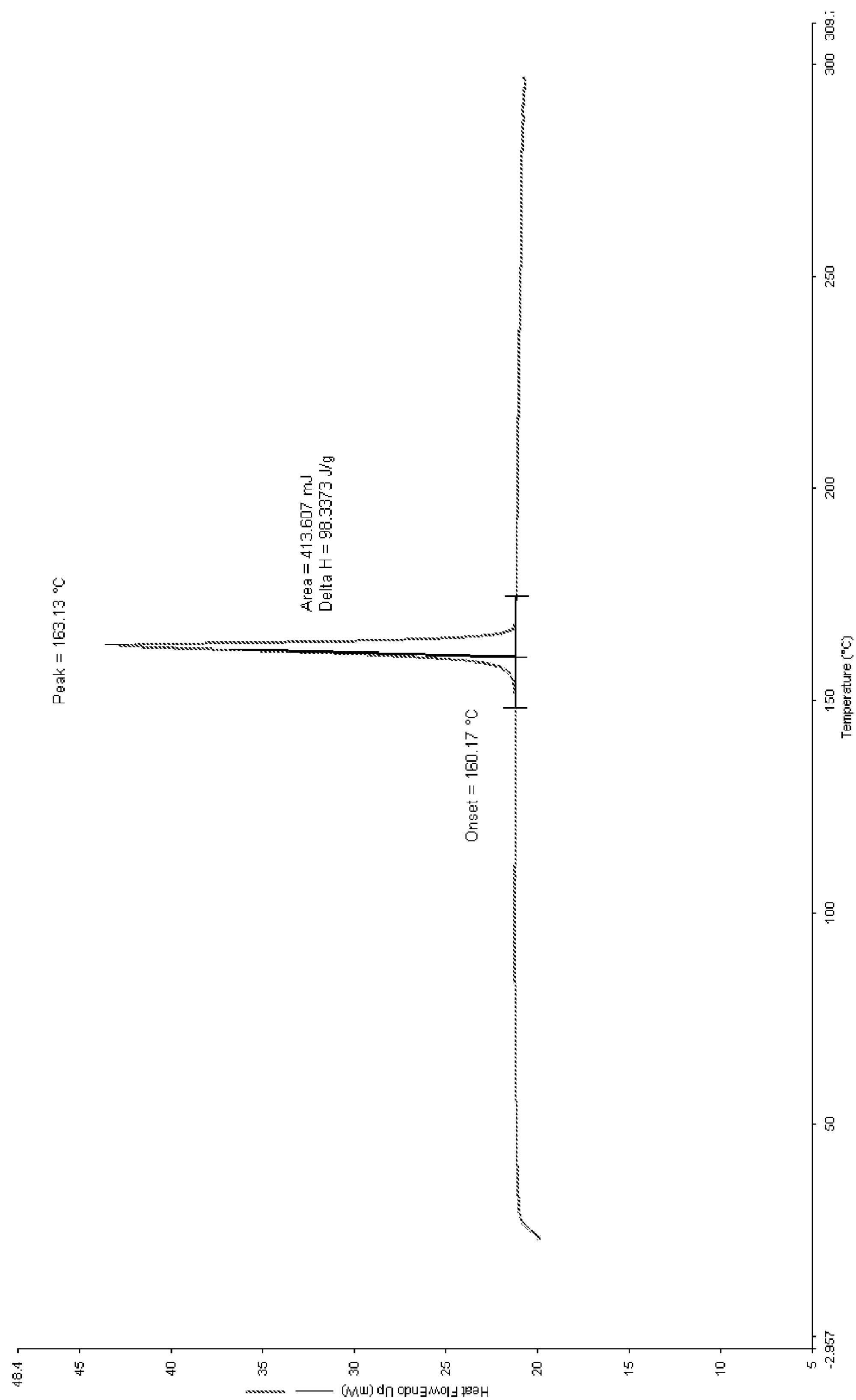
FIG. 5 is a Differential Scanning Calorimetry (DSC) thermogram of Form 2 of Compound 10.

Compound 10 (20 g) was dissolved in hot isopropanol (500 mL). The resulting mixture was cooled and filtered. The precipitate was confirmed by XRPD (FIG. 4, and Table below), DSC (FIG. 5) and IR (FIG. 17) to be crystalline polymorph Form 2 of Compound 10.

Form 2

| No. | Position [°2Theta] | Rel. Int [%} |
|---|---|---|
| 1 | 5.181 | 100 |
| 2 | 9.338 | 15.7 |
| 3 | 10.301 | 9.9 |
| 4 | 11.616 | 3.1 |
| 5 | 12.883 | 60.8 |
| 6 | 15.480 | 37.3 |
| 7 | 16.339 | 43.3 |
| 8 | 17.321 | 10.6 |
| 9 | 17.778 | 6.2 |
| 10 | 18.560 | 36.5 |
| 11 | 18.998 | 12.5 |
| 12 | 19.702 | 34.4 |
| 13 | 20.739 | 5.4 |
| 14 | 22.042 | 46.7 |
| 15 | 23.339 | 21.8 |
| 16 | 23.740 | 13.3 |
| 17 | 24.000 | 28.4 |
| 18 | 25.441 | 16.4 |
| 19 | 25.979 | 2.8 |
| 20 | 28.460 | 10.7 |
| 21 | 29.219 | 11.4 |
| 22 | 29.563 | 17.5 |
| 23 | 30.981 | 4.3 |
| 24 | 31.379 | 15.3 |
| 25 | 32.985 | 6 |
| 26 | 33.357 | 7.4 |
| 27 | 35.121 | 3 |
| 28 | 36.237 | 6.3 |
| 29 | 38.922 | 3.1 |

Preparation of Form 3 of Compound 10

Figure 6:
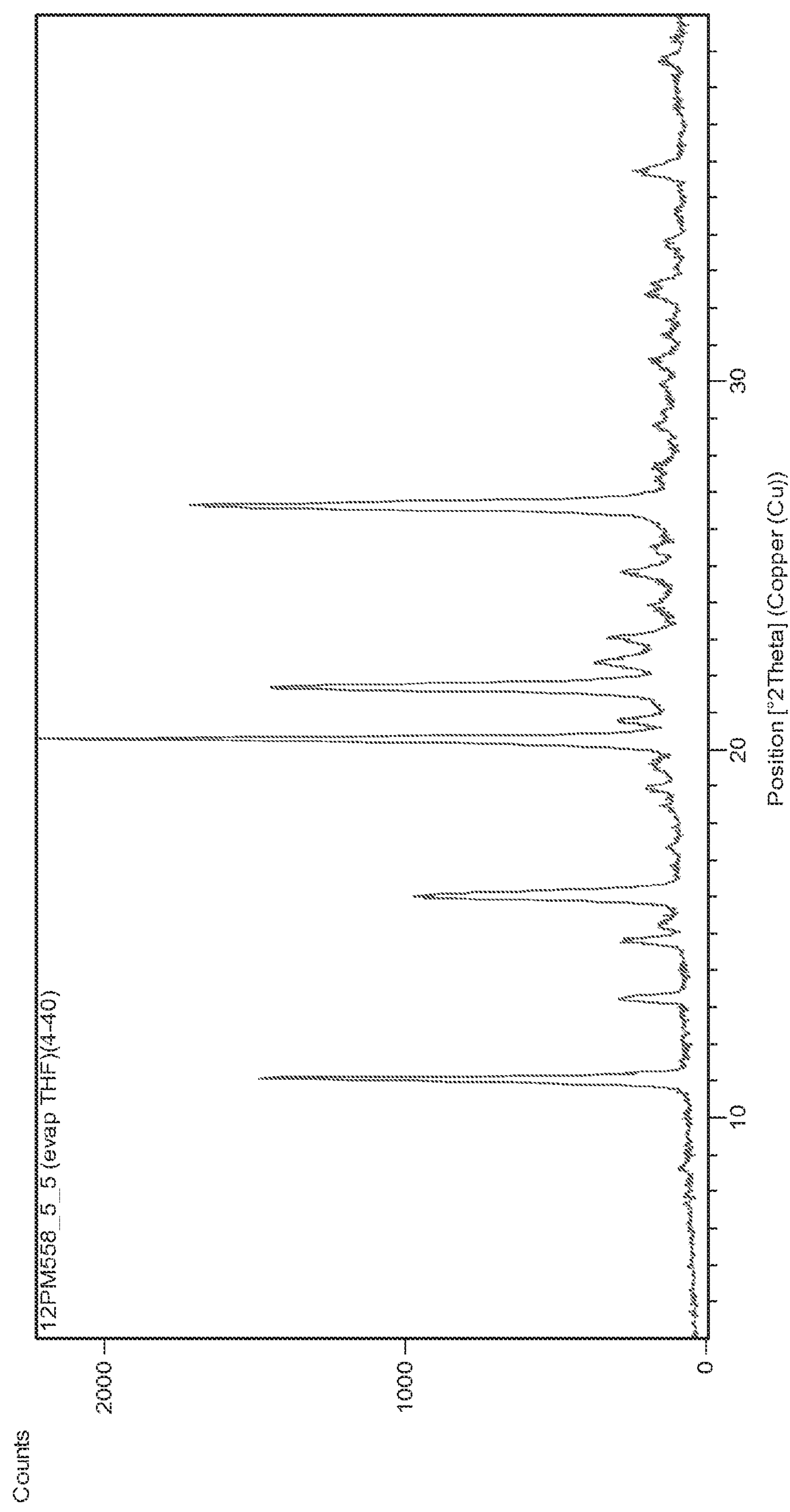
FIG. 6 is an X-ray powder diffraction (XRPD) spectrum of the crystalline polymorph Form 3 of Compound 10.

Compound 10 (50 mg) was dissolved in THF. The solvent was then evaporated to obtain Form 3 of compound, as shown in XRPD (FIG. 6, and Table below).

| Form 3 | | |
|---|---|---|
| No. | Pos. [°2Th.] | Rel. Int. [%] |
| 1 | 8.6551 | 1.69 |
| 2 | 11.0695 | 33.76 |
| 3 | 13.1783 | 7.89 |
| 4 | 14.8069 | 10.16 |
| 5 | 15.1796 | 5.68 |
| 6 | 16.0451 | 56.87 |
| 7 | 17.333 | 3.67 |
| 8 | 18.9513 | 6.27 |
| 9 | 19.5612 | 6.35 |
| 10 | 20.3013 | 51.19 |
| 11 | 20.7959 | 10.72 |
| 12 | 21.6861 | 58.59 |
| 13 | 22.3681 | 14.35 |
| 14 | 23.0482 | 7.54 |
| 15 | 23.8843 | 7.7 |
| 16 | 24.8353 | 10.07 |
| 17 | 25.4458 | 5.67 |
| 18 | 26.6585 | 100 |
| 19 | 28.784 | 5.48 |
| 20 | 30.583 | 6.41 |
| 21 | 31.2709 | 3.15 |
| 22 | 32.35 | 6.44 |
| 23 | 32.7069 | 5.26 |
| 24 | 33.7889 | 4.28 |
| 25 | 35.6672 | 8.71 |
| 26 | 38.7807 | 4.08 |

Preparation of Form 4 of Compound 10

Figure 7:
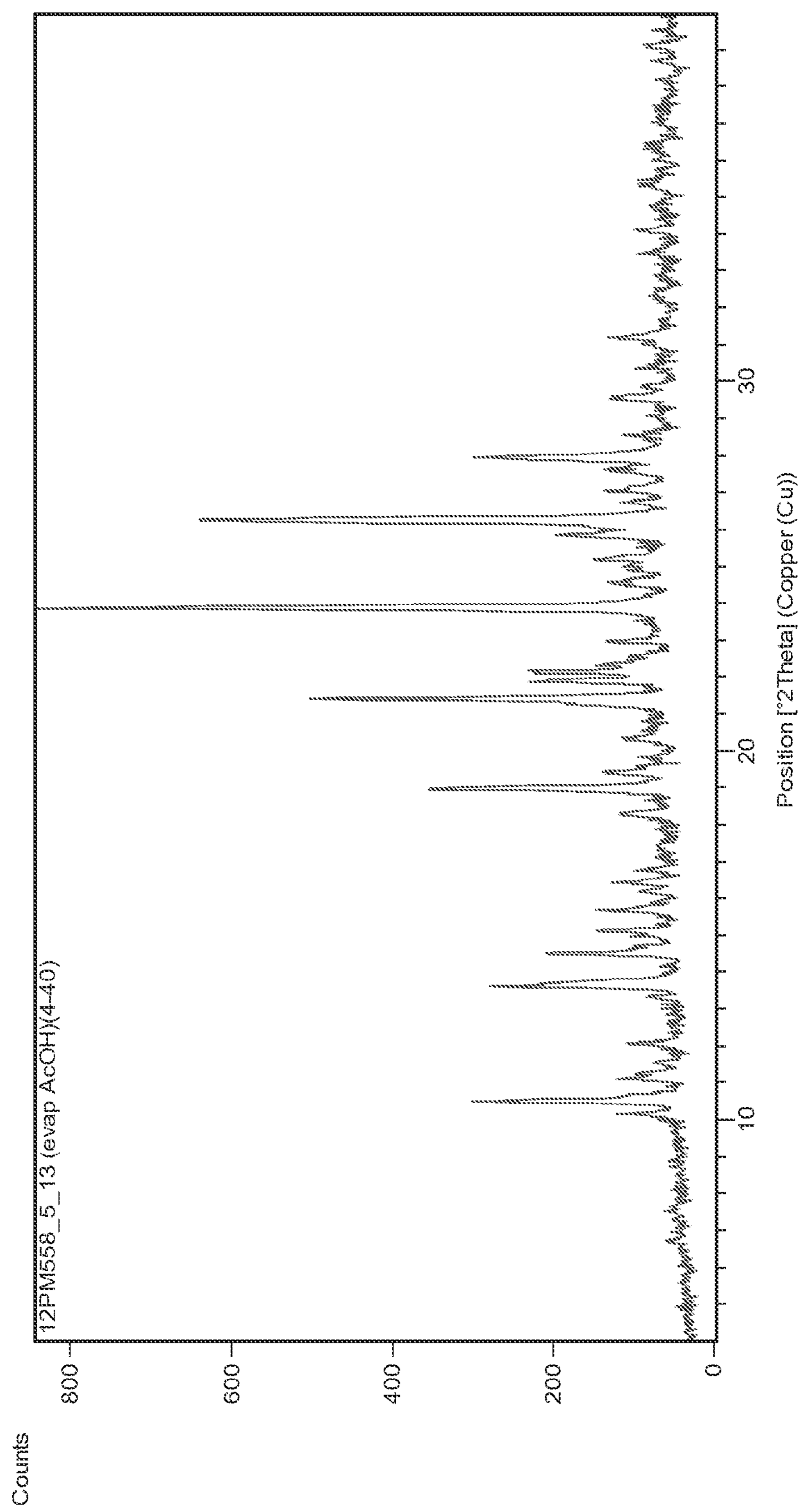
FIG. 7 is an X-ray powder diffraction (XRPD) spectrum of the crystalline polymorph Form 4 of Compound 10.

Compound 10 (50 mg) was dissolved in 300 μL hot acetic acid. Then the resulting supersaturated suspension was filtered in about 100 μl aliquots into 0.5 mL pentane at ambient temperature. When solid was precipitated, excess liquid was decanted off and the solid products were dried under vacuum. XRPD (FIG. 7 and table below) confirm the Form 4.

| Form 4 | | |
|---|---|---|
| No. | Pos. [°2Th.] | Rel. Int. [%] |
| 1 | 10.1566 | 6.99 |
| 2 | 10.4725 | 20.87 |
| 3 | 11.098 | 7.03 |
| 4 | 12.0659 | 8.21 |
| 5 | 13.5976 | 15.93 |
| 6 | 14.502 | 14.08 |
| 7 | 15.1097 | 8.96 |
| 8 | 15.6791 | 9.94 |
| 9 | 16.198 | 6.5 |
| 10 | 16.4293 | 7.72 |
| 11 | 16.7776 | 6.3 |
| 12 | 18.3378 | 10.24 |
| 13 | 18.9548 | 26.39 |
| 14 | 19.4013 | 9.53 |
| 15 | 20.3247 | 7.02 |
| 16 | 21.4229 | 45.02 |
| 17 | 21.8607 | 18.8 |
| 18 | 22.138 | 14.75 |
| 19 | 22.9464 | 7.95 |
| 20 | 23.851 | 95.5 |
| 21 | 24.5112 | 15.82 |
| 22 | 25.213 | 9.33 |

-continued

| Form 4 | | |
|---|---|---|
| No. | Pos. [°2Th.] | Rel. Int. [%] |
| 23 | 25.8148 | 18.29 |
| 24 | 26.2445 | 100 |
| 25 | 27.0431 | 14.55 |
| 26 | 27.5842 | 13.95 |
| 27 | 27.9481 | 38.84 |
| 28 | 28.5474 | 10.74 |
| 29 | 29.5531 | 10.72 |
| 30 | 31.1995 | 10.78 |
| 31 | 34.102 | 7.5 |
| 32 | 35.3142 | 8.46 |
| 33 | 36.3998 | 7.51 |
| 34 | 39.1019 | 5.82 |

Preparation of Form 5 of Compound 10

Figure 8:
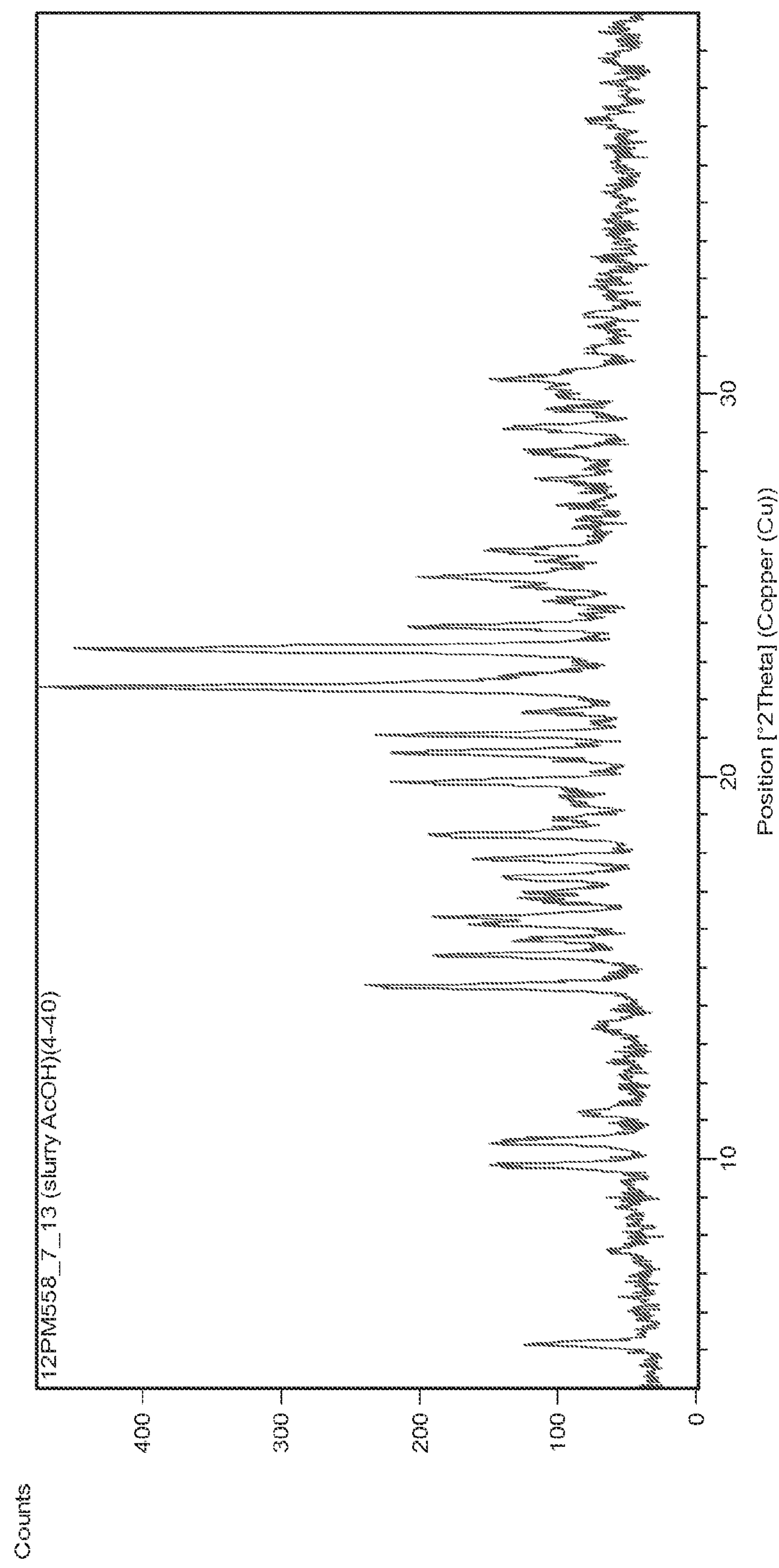
FIG. 8 is an X-ray powder diffraction (XRPD) spectrum of the crystalline polymorph Form 5 of Compound 10.
Figure 9:
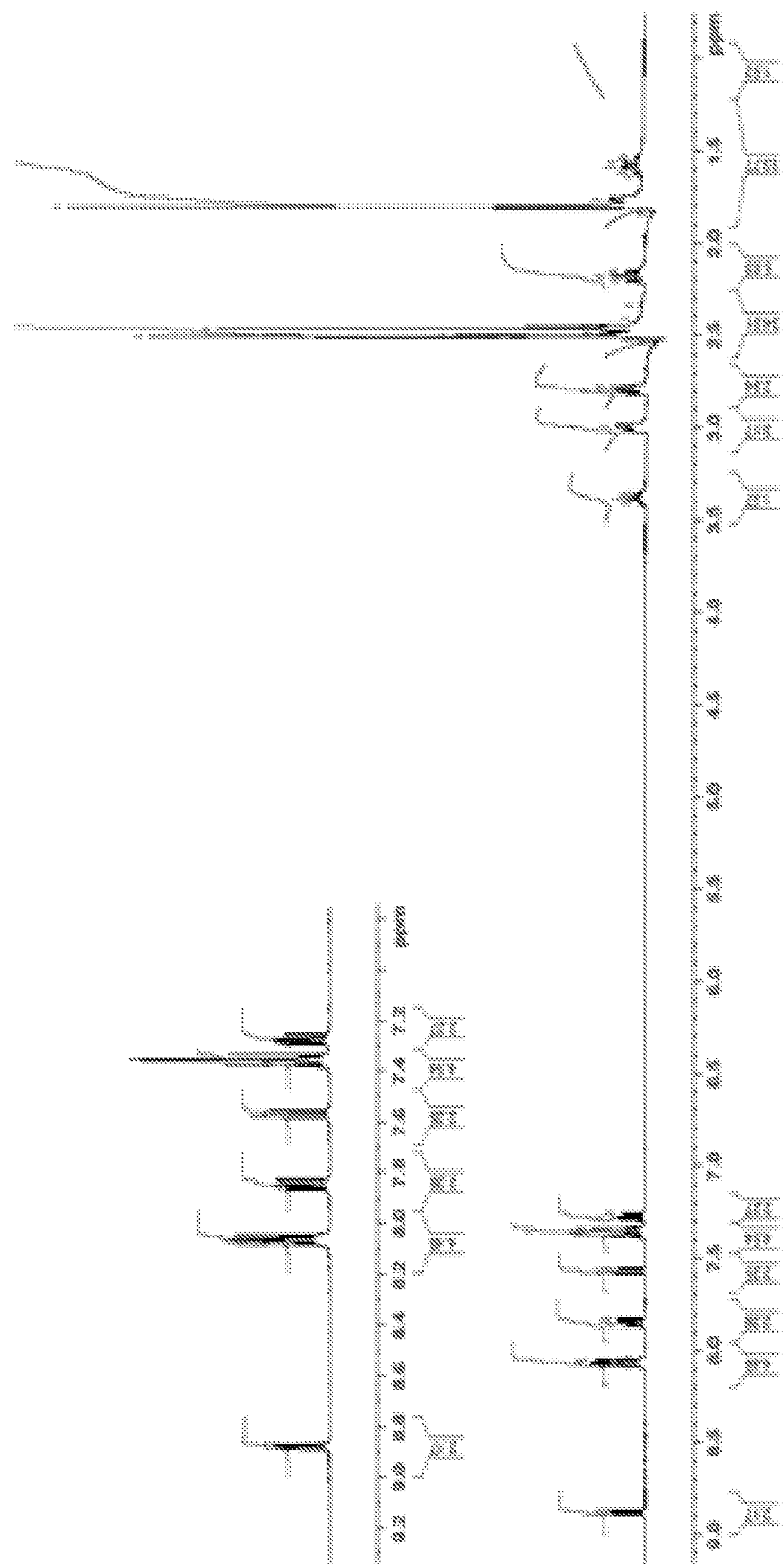
FIG. 9 is a 1H-NMR spectrum of the crystalline polymorph Form 5 of Compound 10.
Figure 10:
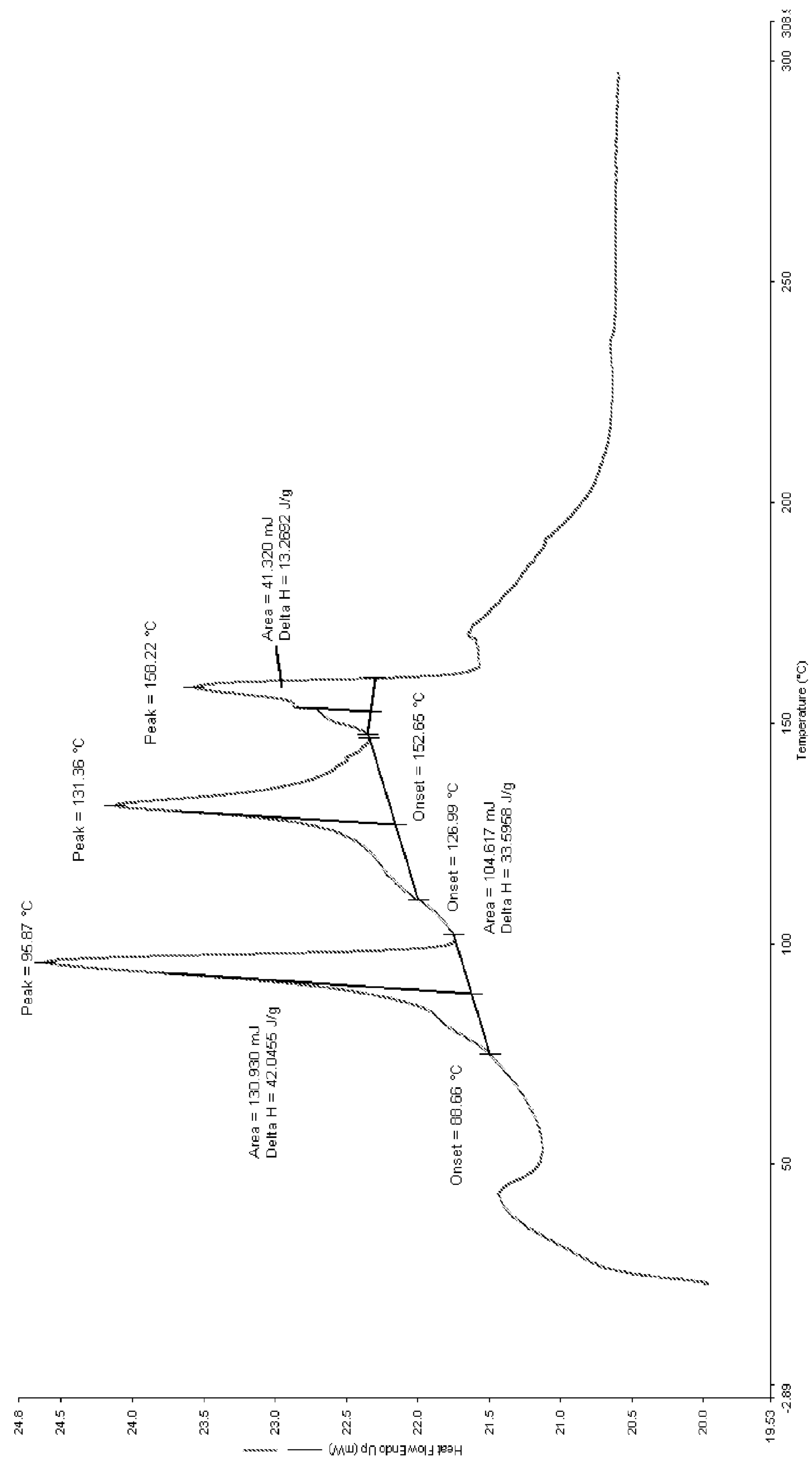
FIG. 10 is a Differential Scanning Calorimetry (DSC) thermogram of the crystalline polymorph Form 5 of Compound 10.

150 mg Compound 10 was heated in 750 mL of acetic acid. The hot suspension was filtered and the resulting solution was allowed to evaporate under nitrogen over 72 hours. The residual oily solid product was dried at 50° C. under vacuum for a further 24 hours. The XRPD (FIG. 8 and Table below), $^{1}$H-NMR (FIG. 9) and DSC spectrum (FIG. 10) confirmed the Form 5 of Compound 10.

| Form 5 | | |
|---|---|---|
| No. | Pos. [°2Th.] | Rel. Int. [%] |
| 1 | 5.1573 | 22.76 |
| 2 | 7.6003 | 17.37 |
| 3 | 9.8226 | 35.83 |
| 4 | 10.4118 | 30.09 |
| 5 | 11.221 | 22.41 |
| 6 | 13.4557 | 14.92 |
| 7 | 14.5118 | 44.71 |
| 8 | 15.3137 | 40.86 |
| 9 | 15.739 | 21.14 |
| 10 | 16.3251 | 20.44 |
| 11 | 16.8318 | 32.66 |
| 12 | 17.3538 | 31.95 |
| 13 | 17.8279 | 29.45 |
| 14 | 18.4845 | 34.61 |
| 15 | 19.8664 | 47.25 |
| 16 | 20.6199 | 46.71 |
| 17 | 21.0772 | 31.74 |
| 18 | 21.7084 | 17.71 |
| 19 | 22.3275 | 100 |
| 20 | 23.3186 | 91.87 |
| 21 | 23.9047 | 38.01 |
| 22 | 25.1972 | 34.6 |
| 23 | 25.9155 | 25.86 |
| 24 | 27.7702 | 15.64 |
| 25 | 28.5113 | 30.71 |
| 26 | 29.1323 | 31.3 |
| 27 | 30.3986 | 22.87 |
| 28 | 37.2028 | 16.01 |

Preparation of Form 2' of Compound 10

Figure 11:
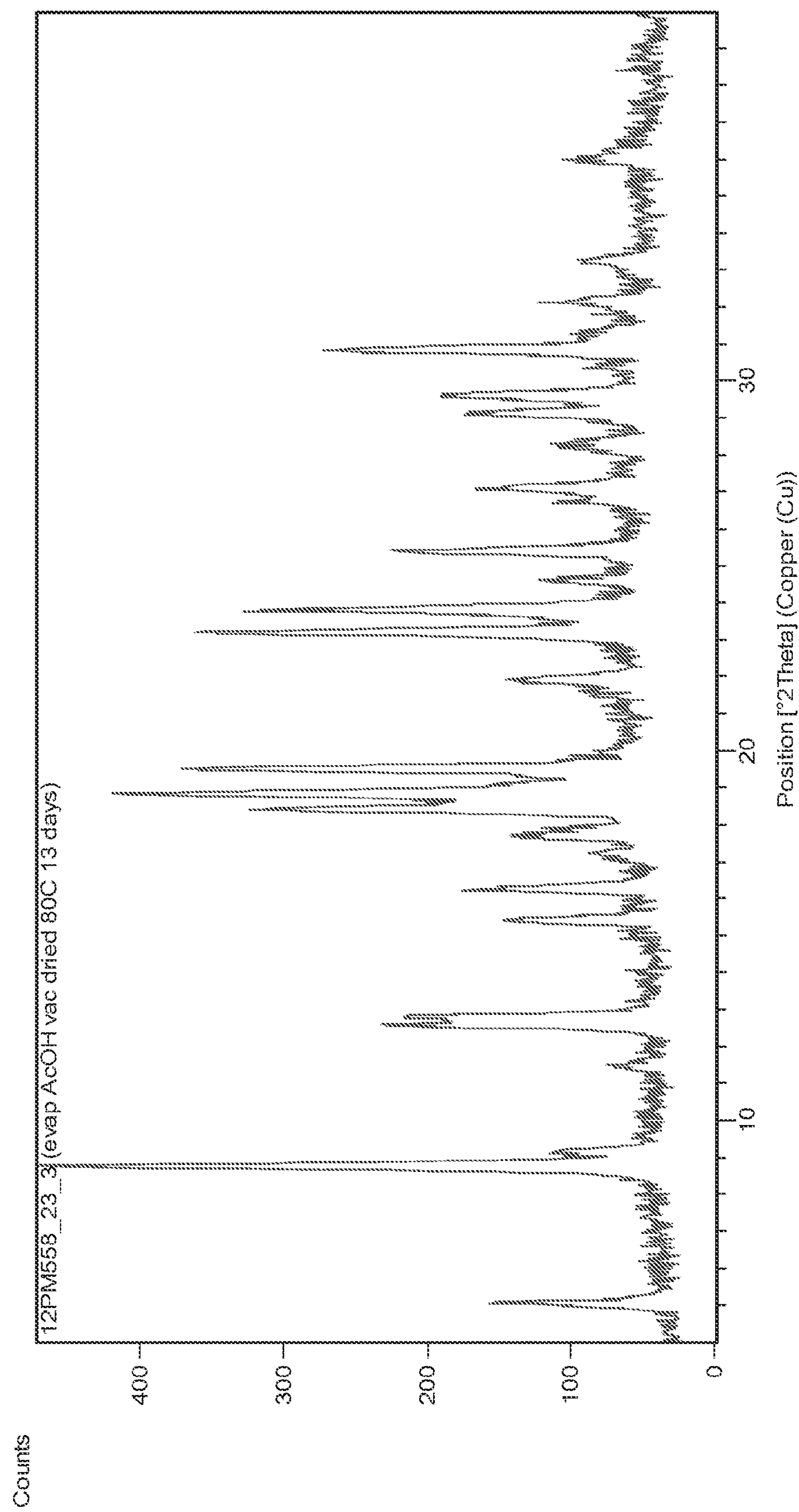
FIG. 11 is an X-ray powder diffraction (XRPD)spectrum of crystalline polymorph Form 2' of Compound 10.
Figure 12:
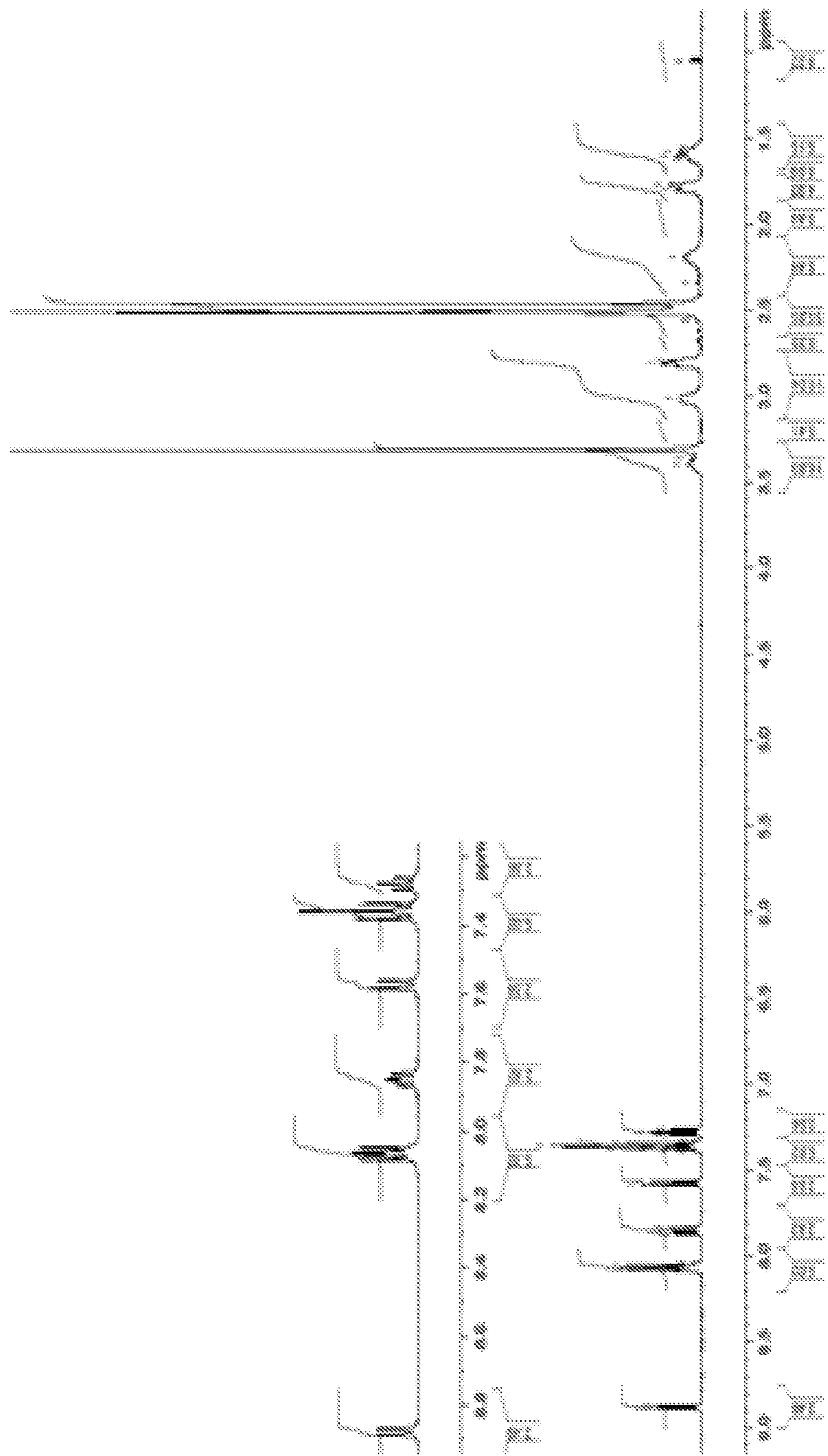
FIG. 12 is a $^{1}$H-NMR spectrum of the crystalline polymorph Form 2' of Compound 10.
Figure 13:
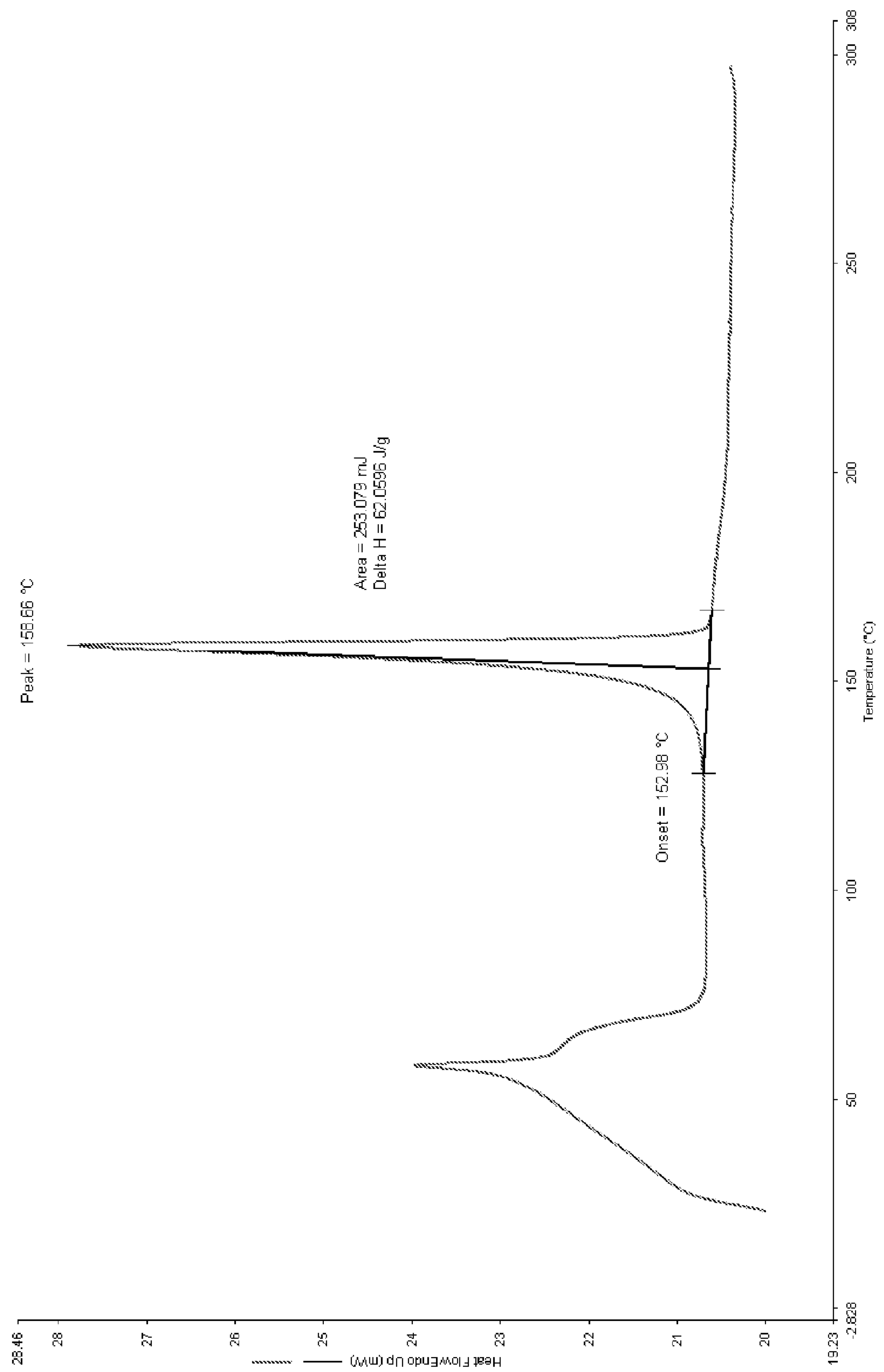
FIG. 13 is Differential Scanning Calorimetry (DSC) thermogram of the crystalline polymorph Form 2' of Compound 10.

Form 5 may convert to a different form (Form 2') which has a similar X-ray pattern to Form 2 on drying (80° C.), as shown in Table below and FIG. 11 (XRPD), FIG. 12 ($^{1}$H-NMR), and FIG. 13 (DSC).

| Form 2' | | |
|---|---|---|
| No. | Pos. [°2Th.] | Rel. Int. [%] |
| 1 | 5.0964 | 14.81 |
| 2 | 8.7824 | 100 |
| 3 | 9.1694 | 12.77 |
| 4 | 11.4795 | 7.47 |
| 5 | 12.5424 | 30.97 |
| 6 | 12.8279 | 30.85 |
| 7 | 15.3913 | 24.36 |
| 8 | 16.23 | 40.29 |
| 9 | 17.1786 | 10.19 |
| 10 | 17.6439 | 15.83 |
| 11 | 18.4299 | 49.92 |
| 12 | 18.8254 | 52.1 |
| 13 | 19.4731 | 65.66 |
| 14 | 21.9515 | 29.9 |
| 15 | 23.1505 | 52.08 |
| 16 | 23.8 | 60.45 |
| 17 | 24.5679 | 15.41 |
| 18 | 25.4109 | 33.72 |
| 19 | 27.0951 | 26.61 |
| 20 | 28.294 | 26.09 |
| 21 | 29.0906 | 28.75 |
| 22 | 29.6204 | 38.99 |
| 23 | 30.8262 | 60.52 |
| 24 | 32.159 | 22.39 |
| 25 | 33.2566 | 17.55 |
| 26 | 35.9669 | 14.23 |

Preparation of Form 6 of Compound 10

Figure 18:
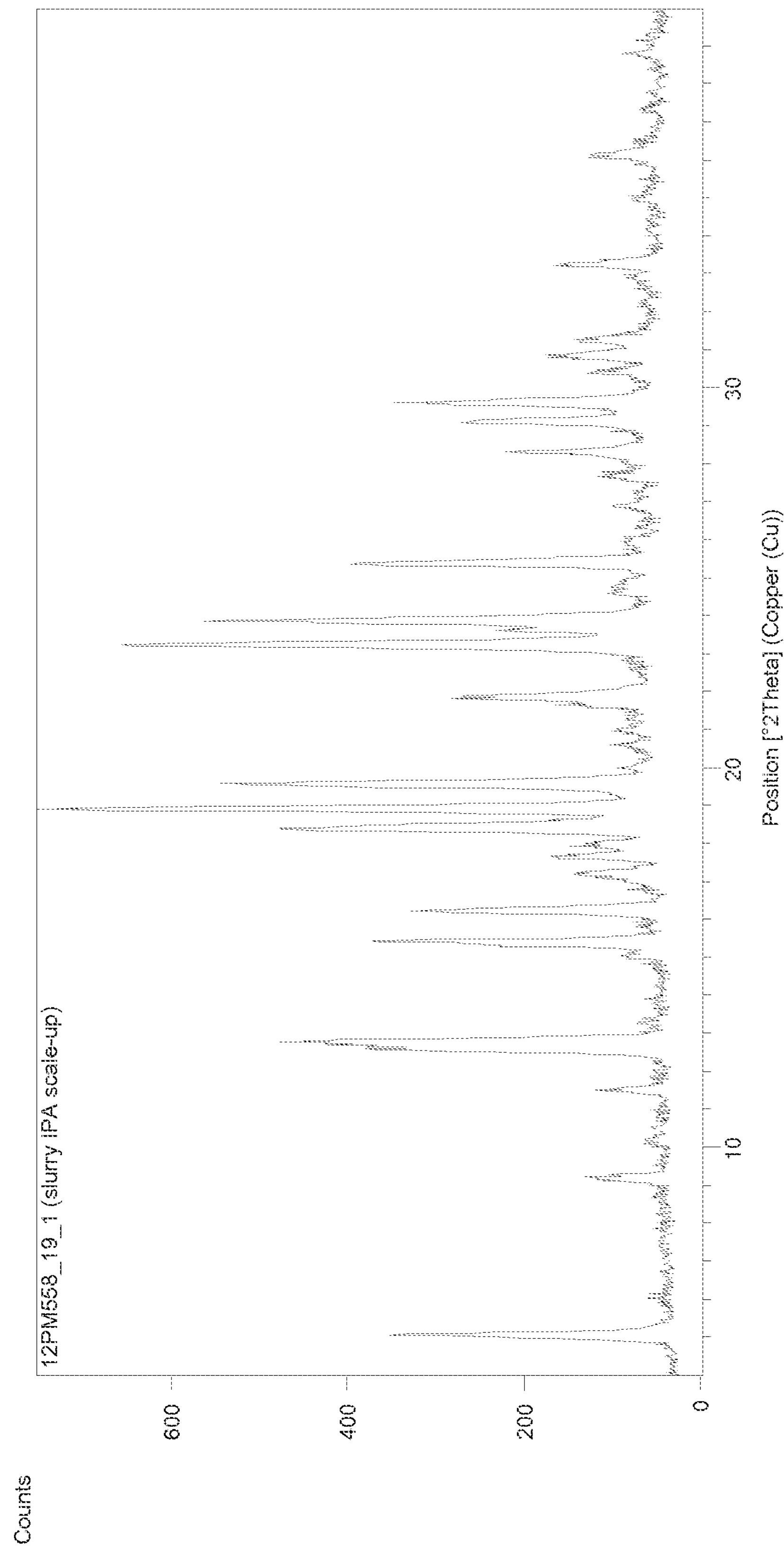
FIG. 18 is an X-ray powder diffraction (XRPD) spectrum of crystalline polymorph Form 6 of Compound 10.

Compound 10 (50 mg) was dissolved in hot isopropanol (1 mL). The resulting mixture was cooled and filtered. The precipitate was confirmed by XRPD (FIG. 18, and Table below) and DSC (FIG. 5) to be crystalline polymorph Form 6 of Compound 10.

| Form 6 | | |
|---|---|---|
| No. | Pos. [°2Th.] | Rel. Int. [%] |
| 1 | 4.9428 | 100 |
| 2 | 10.1075 | 18.05 |
| 3 | 12.473 | 30.17 |
| 4 | 12.7361 | 53.37 |
| 5 | 15.2935 | 67.38 |
| 6 | 16.1314 | 22.48 |
| 7 | 18.2588 | 28.42 |
| 8 | 18.8106 | 66.84 |
| 9 | 19.4499 | 30.74 |
| 10 | 20.4997 | 19.91 |
| 11 | 21.7780 | 24.74 |
| 12 | 23.1042 | 39.67 |
| 13 | 23.7388 | 40.91 |
| 14 | 25.2790 | 38.06 |
| 15 | 29.0161 | 20.63 |
| 16 | 29.4869 | 19.98 |

Preparation of Form 7 of Compound 10

Figure 19:
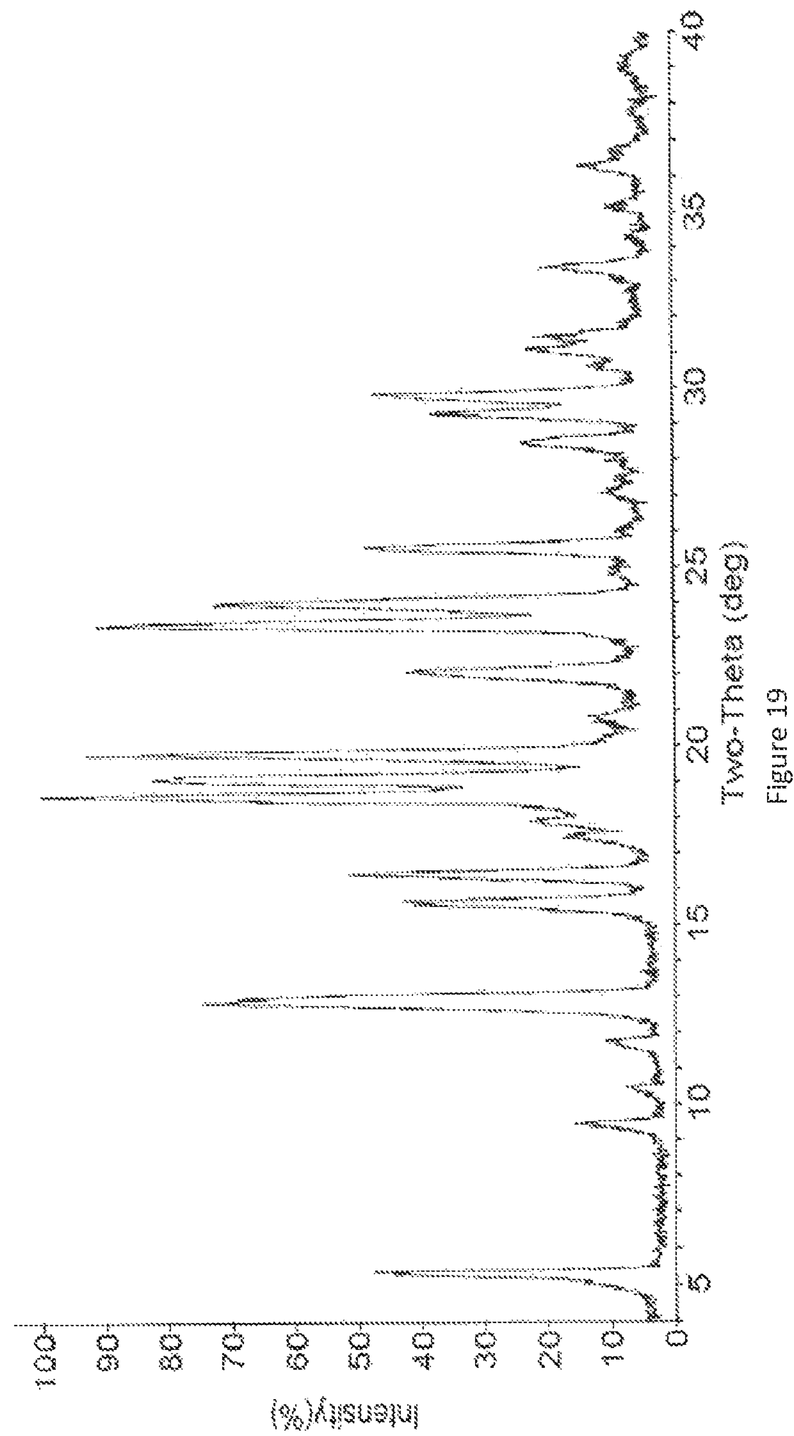
FIG. 19 is an X-ray powder diffraction (XRPD) spectrum of crystalline polymorph Form 7 of Compound 10.

Compound 10 (50 g) was dissolved in hot isopropanol (1000 mL). The resulting mixture was cooled and filtered. The precipitate was confirmed by XRPD (FIG. 19, and Table below) to be crystalline polymorph Form 7 of Compound 10.

| Form 7 | | |
|---|---|---|
| No. | Pos. [°2Th.] | Rel. Int. [%] |
| 1 | 5.355 | 47.1 |
| 2 | 9.441 | 14.5 |
| 3 | 12.880 | 75.7 |
| 4 | 15.678 | 40.8 |
| 5 | 16.421 | 49.3 |
| 6 | 17.441 | 14.4 |
| 7 | 17.900 | 19.8 |
| 8 | 18.659 | 100.0 |
| 9 | 19.100 | 81.4 |
| 10 | 19.781 | 92.4 |
| 11 | 22.081 | 37.5 |
| 12 | 23.401 | 90.3 |
| 13 | 23.982 | 70.3 |
| 14 | 25.580 | 44.9 |
| 15 | 28.461 | 17.5 |
| 16 | 29.321 | 34.4 |
| 17 | 29.857 | 43.6 |
| 18 | 30.618 | 7.8 |
| 19 | 31.101 | 17.6 |
| 20 | 31.438 | 18.5 |
| 21 | 33.401 | 17.0 |
| 22 | 35.143 | 6.1 |
| 23 | 36.280 | 11.0 |

X-Ray Powder Diffraction (XRPD). Approximately 2 mg of sample was gently compressed on the XRPD zero back ground single obliquely cut silica sample holder. The sample was then loaded into a D/MAX 2200 X-ray powder diffractometer (Rigaku) or a Philips X-Pert MPD diffractometer and analyzed using the following experimental conditions (Tube anode: Cu; Generator tension: 40 kV; Tube current: 40 mA; Wavelength alpha1: 1.54056 Å; Wavelength alpha2: 1.5444 Å; Start angle [2 theta]: 5; End angle [2 theta]: 50; and Continuous scan). For suspected novel forms a slightly slower scan speed was used over a range of 4-40° 2θ.

Raman Spectroscopy. Samples were analyzed by a Nicolet Almega XR Dispersive Raman Microscope for its Raman spectrum using the following conditions (Exposure Time: 1.0 s; Acquisition No: 10; Pinhole Size: 25, 50 or 100 μm; Wavelength range: 2000 to 300 $cm^1$ (single grating); Laser: He—Ne 780 nm 100% power; Objective: 20×/0.40 or 50×/0.75 (magnifier/numerical aperture number)). Then the measured Raman spectra were corrected by baseline subtraction using the software OMNIC™ v7.3.

Simultaneous Thermal Analysis (STA). Approximately 5 mg of sample was accurately weighed into a ceramic crucible and it was placed into the chamber of Perkin-Elmer STA 600 TGA/DTA analyzer at ambient temperature. The sample was then heated at a rate of 10° C./min from 25° C. to 300° C. during which time the change in weight was monitored as well as DTA signal. The purge gas used was nitrogen at a flow rate of 20 $cm^3$/min.

Differential Scanning Calorimetry (DSC). Approximately, 5 mg of each sample was weighed into an aluminum DSC pan and sealed non-hermetically with an aluminum lid. The sample was then loaded into a Perkin-Elmer Jade DSC and held at 25° C. Once a stable heat-flow response was obtained, the sample was then heated to 300° C. at a scan rate of 10° C./min and the resulting heat flow response was monitored. A 20 $cm^3$/min helium purge was used. Prior to analysis, the instrument was temperature and heat flow verified using an indium standard.

Biological Activities

Chronic Constriction Injury (CCI) Model of Neuropathic Pain in Rat. The CCI model is one of the most commonly used mono-neuropathic pain model firstly described in details by Bennett and Xie (Bennett G J, Xie Y K. Pain. 1988; 33(1):87-107). It mimics important clinical chronic pain symptoms such as mechanical allodynia and thermal hyperalgesia. Chronic constriction injury of the sciatic nerve was produced by tying four loose ligatures around the left sciatic nerve according to the method of Bennett and Xie. This procedure resulted in tactile allodynia in the left hindpaw. Calibrated von Frey filaments were used to determine the lowest mechanical (tactile) threshold required to evoke a brisk paw withdrawal reflex in the rat hindpaws. Rats were allowed to acclimatize in wire mesh cages for 15-20 min prior to von Frey testing. Assessment of paw withdrawal thresholds (PWTs) using von Frey filaments was undertaken prior to CCI-surgery (pre-surgery baseline on day 0). Before the drug dosing on day 14, the pre-dose baseline was recorded for each rat. Rats were included in the study only if they did not exhibit motor dysfunction (e.g., paw dragging or dropping) and their PWT was below to 4 g. Drug-naïve CCI-rats (n=4-6 per group) were used. The oral (PO) gavage vehicle was either 10% (w/v) Povidone K25 in water for PO dosing, or 18% (w/v) CrosPovidone in water for PO dosing, or 0.5% CMC-Na/0.1% Tween 80 in distilled water for PO dosing. The positive control gabapentin was dissolved in the vehicle and orally given at 100 mg/kg (by oral gavage). Test article was dissolved or suspended in the vehicle and orally given at 25, 50, 100 and 150 mg/kg. Each CCI-rat was administered a single oral dose of test article, gabapentin or vehicle control, 2 hours before assessment of PWT.

Figure 14:
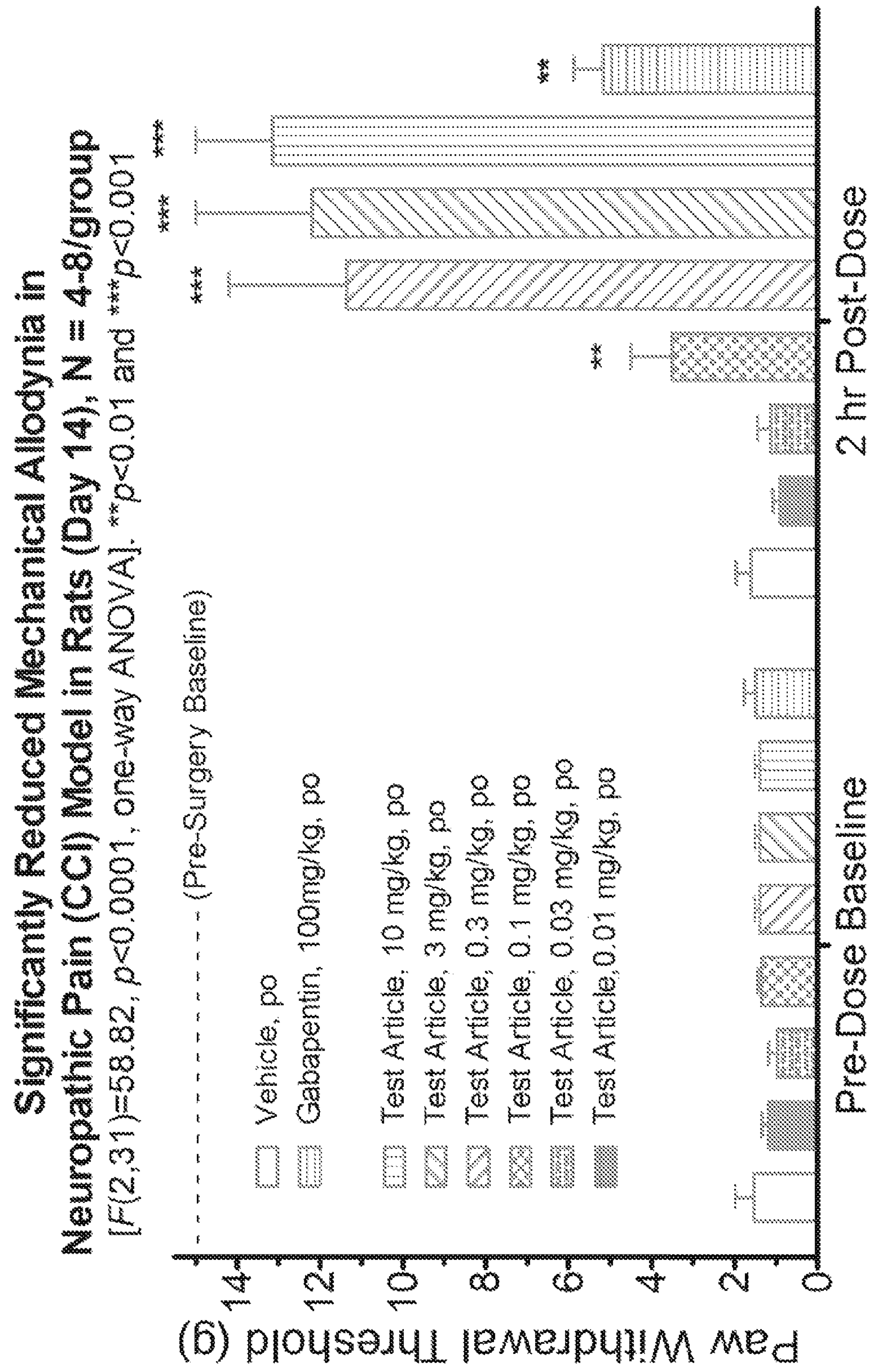
FIG. 14 is a graph showing oral dose-dependent reduction of neuropathic pain in rat model of neuropathic (CCI) pain with an inventive compound compared to vehicle (negative control) and gabapentin (positive control).

The results have demonstrated, as shown in FIG. 14, that oral administration of The compound of current invention of present invention significantly reduced mechanical allodynia in CCI rats of neuropathic pain model in a dose-dependent manner, and it is more than 100 time more potent than positive control gabapentin, the current gold standard medication for neuropathic pain, in this neuropathic pain model. Of note, CCI-rats dosed with gabapentin have shown drowsiness or motor incoordination, which is consistent with known side effect of gabapentin. However, no such effect or other abnormality was observed in CCI-rats dosed with the compound of current invention.

Spinal Nerve Ligation (SNL) Mono-Neuropathic Pain Model in Rat. The surgical procedure will be performed according to the method firstly described by Kim and Chung (Kim S H, Chung J M. Pain. 1992; 50(3):355-63.). This procedure will result in tactile allodynia in the left hindpaw. Rats will be included in the study only if they do not exhibit motor dysfunction (e.g., paw dragging or dropping) and their PWT is below to 4.0 g. The dose-response anti-allodynia effects of test compound: on day 14 after surgery, rats were treated with test article at one of four doses, vehicle or positive control by oral gavage, and PWT was determined by calibrated von Frey filaments at time points of 0 (right before the drug dosing, Pre-Dose Baseline), 0.5, 1, 2, 4 and 6 hr. The anti-allodynia effects of repeated administration of test article: Administration of test article was started on day 7 after surgery, once a day for 7 days. PWT was determined by calibrated von Frey filaments, 2 hour after test article dosing each day. After 7 days dosing, the measurement were continued, every other day without compound dosing for another 7 days. PWT was determined at the time points as given above. The results have demonstrated that oral administration of the compound of current invention of present invention significantly reduced mechanical allodynia in SNL rats of neuropathic pain model in a dose-dependent manner.

Figure 15:
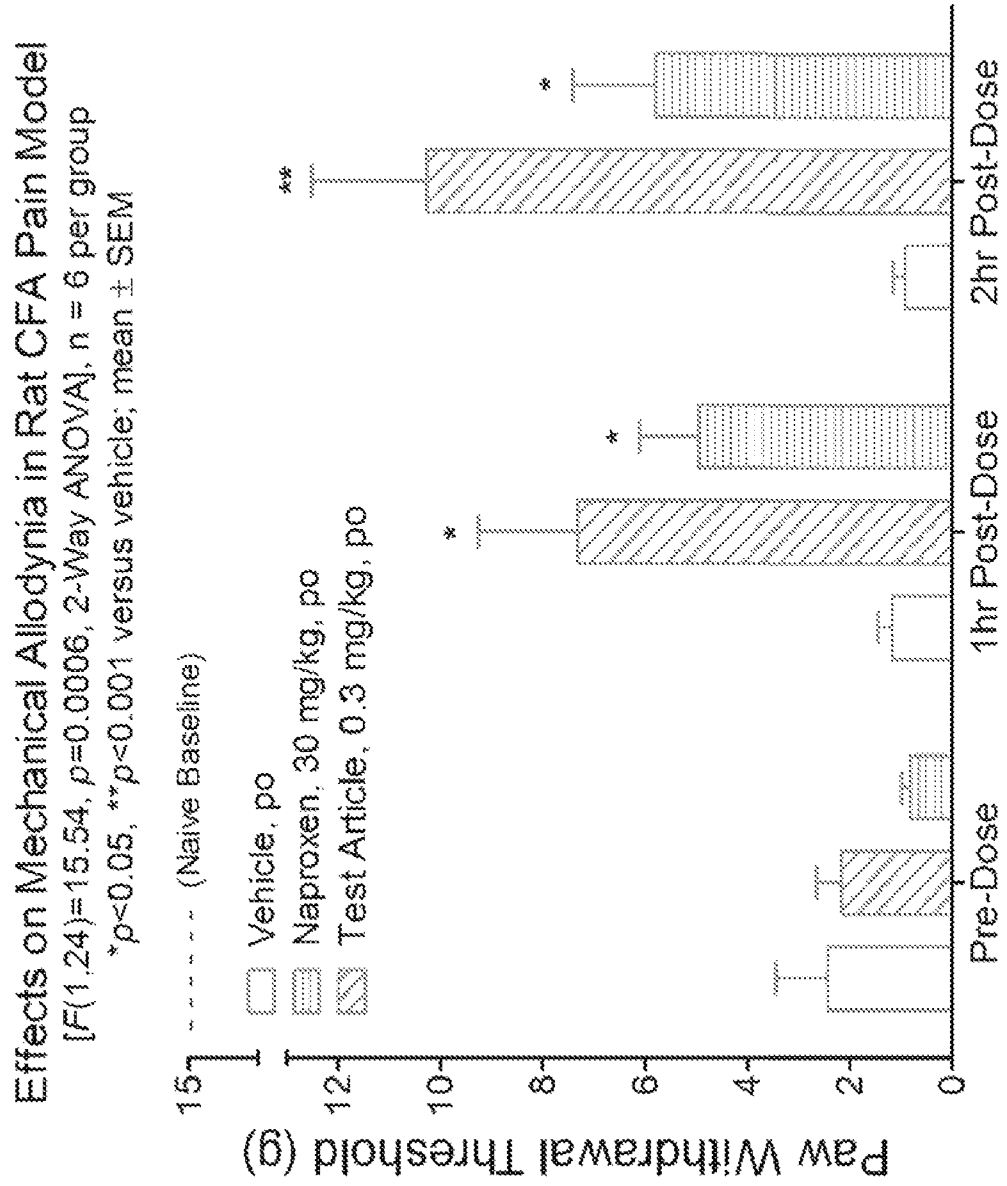
FIG. 15 is a graph showing oral dose reduction of pain in rat model of CFA-induced inflammatory pain with an inventive compound compared to vehicle (negative control) and naproxen (positive control) naproxen.
Figure 16:
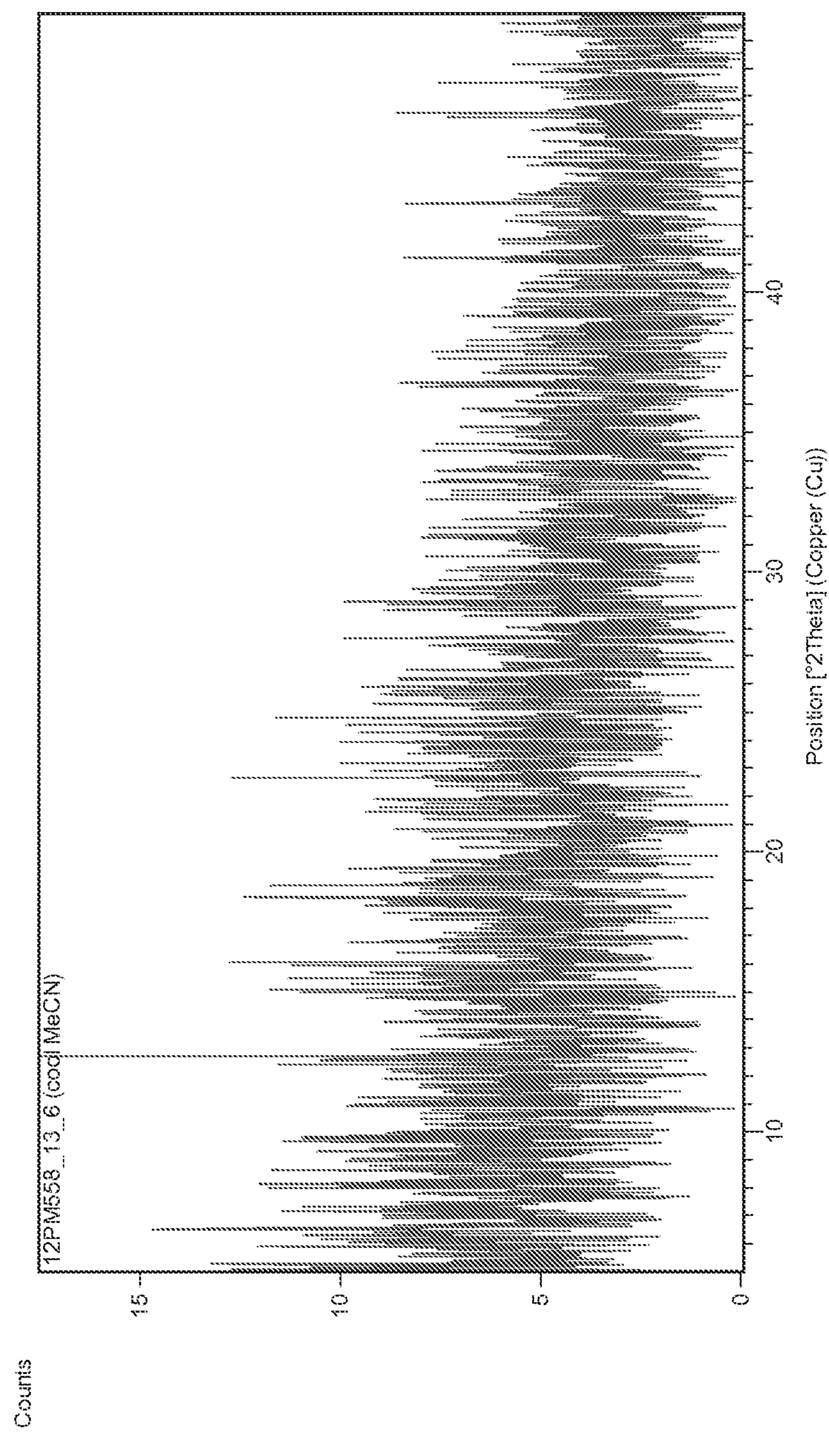
FIG. 16 is an X-Ray Powder Diffraction (XRPD) spectrum of the amorphous form of Compound 10.

Rat CFA-Induced Inflammatory Pain Model. Hyperalgesia was induced by subcutaneously injecting 50 L of CFA (Sigma-Aldrich, St. Louis, Mo., USA) into the plantar surface of the left hind paw of the rats using a 30-gauge hypodermic needle under sevoflurane anesthesia. The classical signs of inflammation, including edema and redness, for up the last day of tests were recorded. To assess the effect of test article on CFA-induced inflammatory pain, the rats were anesthetized with sevoflurane 3 hours after CFA injection and then orally dosed with test article (n=6) or vehicle (n=6) or positive control. Paw withdrawal latencies (thermal hyperalgesia) are measured before and at 2 and 4 hours after CFA injection. Mechanical thresholds were also measured in the same way with either the compound of current invention (n=6) or vehicle (n=6) or positive control, Naproxen (n=6) at similar different time points (for example, 1 and 3 hour). The noxious heat and mechanical thresholds were separately measured in each group of rats. The threshold was measured 3-5 times in each rat and then averaged. Stimulus interval was 5 min. The analgesic effect of the compound of current invention on this rat CFA-induced inflammatory pain model is given in FIG. 15, where it clearly shown that the compound of current invention is more efficacious than positive control Naproxen in relieving the pain in this rat pain model.

Pharmaceutical Compositions of the Invention

In one aspect, the present invention provides pharmaceutical compositions containing one or more compounds of the present invention with stable polymorphic form of current invention.

The present pharmaceutical compositions contain a therapeutically effective amount of the present invention, preferably in purified form, together with a suitable amount of a pharmaceutically acceptable vehicle and/or one or more excipients, so as to provide a solid form for proper administration to a patient. When administered to a patient, the present compound with a novel stable polymorphic form and the pharmaceutically acceptable vehicles are preferably sterile. Water is a preferred vehicle when a compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations that can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No.

5,698,155). Other examples of suitable pharmaceutical vehicles have been described in the art (see Remington: The Science and Practice of Pharmacy, Philadelphia College of Pharmacy and Science, 20$^{th}$ Edition, 2000).

For topical administration the compound may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent such as another anti-cancer agent.

In some embodiments, the present compound with a novel stable polymorphic form, are formulated in accordance with routine procedures as a pharmaceutical composition adapted for intravenous administration to human beings. Typically, compounds for intravenous administration are solutions in sterile isotonic aqueous buffer. For injection, the present compound with a novel stable polymorphic form may be formulated in aqueous solutions, preferably, in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the present compound with a novel stable polymorphic form, are administered by infusion, it can be dispensed, for example, with an infusion bottle containing sterile pharmaceutical grade water or saline. When the present compound with a novel stable polymorphic form are administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the invention with a pharmaceutically acceptable vehicle. In some embodiments, the pharmaceutically acceptable vehicle is a liquid such as alcohol, water, polyethylene glycol or a perfluorocarbon. Optionally, another material may be added to alter the aerosol properties of the solution or suspension of compounds disclosed herein. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

The present compound with a novel stable polymorphic form may also be formulated in rectal or vaginal pharmaceutical compositions such as suppositories or retention enemas, e.g., containing conventional suppository bases such as cocoa butter or other glycerides.

In addition to the formulations described previously, the present compound with a novel stable polymorphic form may also be formulated as a depot preparation. Such long acting formulations may be administered by implantation (for example, subcutaneously or intramuscularly) or by intramuscular injection. Thus, for example, the present compound with a novel stable polymorphic form may be formulated with suitable polymeric or hydrophobic materials (for example, as an emulsion in an acceptable oil) or ion exchange resins, or as sparingly soluble derivatives, for example, as a sparingly soluble salt.

Therapeutic Doses

The present compound with a novel stable polymorphic form and a pharmaceutically acceptable vehicle is provided, will generally be used in an amount effective to treat or prevent diseases or disorders including one or more of acute pain, chronic pain, neuropathic pain, inflammatory pain, radicular pain, sciatica, back pain, head pain, neck pain, severe or intractable pain, post surgical pain, visceral pain, cancer pain, osteoarthritis pain, peripheral neuropathy, nociceptive pain, breakthrough pain, migraine, angina, vascular disease, arteriosclerosis, sleep disorders, metabolic disorders, gastrointestinal disease, prostate tumor or cancer, schizophrenia, drug dependence, tinnitus, dementia, asthma, cluster headaches, trigeminal neuralgia, herpetic neuralgia, general neuralgias, epilepsy, neurodegenerative disorders, arthritis, anxiety, depression, myotonia, arrythmia, movement disorders, neuroendocrine disorders, ataxia, multiple sclerosis, irritable bowel syndrome, incontinence, postherpetic neuralgia, diabetic neuropathy, or cancer, contraception, nervous system injury, seizure, convulsion, Huntington's chorea, Alzheimer' disease, autoimmune disease, tremor, Parkinson's diseases, Amyotrophic Lateral Sclerosis (ALS), retinopathy, neoplasm, inflammation, cranial neuropathy, type 1 or type 2 diabetes, hyperaldosteronemia, preterm labor, urinary incontinence, and brain aging.

The amount of the present compound with a novel stable polymorphic form that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of the present compound with a novel stable polymorphic form administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiment, the present compound with a novel stable polymorphic form are delivered by oral sustained release administration. Dosing may be repeated intermittently, may be provided alone or in combination with other drugs and may continue as long as required for effective treatment of the disease state or disorder.

Suitable dosage ranges for oral administration to a patient in need depend on the potency of the present compound with a novel stable polymorphic form, but are generally between about 0.005 mg to about 100 mg of a compound of the invention per kilogram body weight; more preferably, between about 0.005 mg to about 50 mg of a compound of the invention per kilogram body weight; still more preferably, between about 0.005 mg to about 20 mg of a compound of the invention per kilogram body weight; still more preferably, between about 0.01 mg to about 5 mg of a compound of the invention per kilogram body weight; and the patient is an animal; more preferably, a mammal; and most preferably, a human; still more preferably, between about 0.02 mg to about 0.2 mg of a compound of the invention per kilogram body weight; still more preferably, between about 0.1 mg to about 14 mg per day of a compound of the invention; and the patient is an animal; more preferably, a mammal; and most preferably, a human. Dosage ranges may be readily determined by methods known to the artisan of ordinary skill.

Suitable dosage ranges for intravenous (i.v.) administration to a patient in need are about 0.001 mg to about 20 mg per kilogram body weight; more preferably, between about 0.01 mg to about 5 mg of a compound of the invention per kilogram body weight; and the patient is an animal; more preferably, a mammal; and most preferably, a human. Suitable dosage ranges for intranasal administration are generally about 0.001 mg/kg body weight to about 5 mg/kg body weight; more preferably, between about 0.005 mg to about 5 mg of a compound of the invention per kilogram body weight; and the patient is an animal; more preferably, a mammal; and most preferably, a human. Suppositories generally contain about 0.001 milligram to about 15 milligrams of a compound of the invention per kilogram body weight and comprise active ingredient in the range of about 0.5% to about 10% by weight. Recommended dosages for intradermal, intramuscular, intraperitoneal, subcutaneous, epidural, sublingual or intracerebral administration to a patient in need are in the range of about 0.001 mg to about 80 mg per kilogram of body weight; and the patient is an animal; more preferably, a mammal; and most preferably, a human. Effective doses may be extrapolated from dose-response curves derived from in vitro or animal model test systems. Such animal models and systems are well-known in the art.

The present compound with a novel stable polymorphic form are preferably assayed in vitro and in vivo, for the desired therapeutic or prophylactic activity, prior to use in humans. For example, in vitro assays can be used to determine whether administration of a specific compound of the invention or a combination of compounds is preferred for the aforementioned diseases or disorder or conditions. The present compound with a novel stable polymorphic form may also be demonstrated to be effective and safe using animal model systems.

Preferably, a therapeutically effective dose of the present compound with a novel stable polymorphic form will provide therapeutic benefit without causing substantial toxicity. Toxicity of the present compound with a novel stable polymorphic form may be determined using standard pharmaceutical procedures and may be readily ascertained by the skilled artisan. The dose ratio between toxic and therapeutic effect is the therapeutic index. The present compound with a novel stable polymorphic form generally exhibit particularly high therapeutic indices in treating associated disease and disorders or conditions. The dosage of the present compound with a novel stable polymorphic form will preferably be within a range of circulating concentrations that include an effective dose with little or no toxicity.

Combination Therapy

In certain embodiments of the present invention, the present compound with a novel stable polymorphic form can be used in combination therapy with at least one additional active or therapeutic agent. The present compound with a novel stable polymorphic form and the at least one additional active or therapeutic agent can act additively or, more preferably, synergistically. In some embodiments, the present compound with a novel stable polymorphic form is administered concurrently, sequentially, or separately with the administration of another therapeutic agent. Exemplary active agents include, but are not limited to, aceglatone, aclarubicin, altretamine, aminoglutethimide; 5-aminogleavulinic acid, amsacrine, anastrozole, ancitabine hydrochloride, 17-1a antibody, antilymphocyte immunoglobulins, antineoplaston a10, asparaginase, pegaspargase, azacitidine, azathioprine, batimastat, benzoporphyrin derivative, bicalutamide, bisantrene hydrochloride, bleomycin sulphate, brequinar sodium, broxuridine, busulphan, campath-ih, caracemide, carbetimer, carboplatin, carboquone, carmofur, carmustine, chlorambucil, chlorozotocin, chromomycin, cisplatin, cladribine, *corynebacterium parvum*, cyclophosphamide, cyclosporin, cytarabine, dacarbazine, dactinomycin, daunorubicin hydrochloride, decitabine, diaziquone, dichlorodiethylsulphide, didemnin b., docetaxel, doxifluridine, doxorubicin hychloride, droloxifene, echinomycin, edatrexate, elliptinium, elmustine, enloplatin, enocitabine, epirubicin hydrochloride, estramustine sodium phosphate, etanidazole, ethoglucid, etoposide, fadrozole hydrochloride, fazarabine, fenretinide, floxuridine, fludarabine phosphate, fluorouracil, flutamide, formestane, fotemustine, gallium nitrate, gencitabine, gusperimus, homoharringtonine, hydroxyurea, idarubicin hydrochloride, ifosfamide, ilmofosine, improsulfan tosylate, inolimomab, interleukin-2; irinotecan, jm-216, letrozole, lithium gamolenate, lobaplatin, lomustine, lonidamine, mafosfamide, meiphalan, menogaril, mercaptopurine, methotrexate, methotrexate sodium, miboplatin, miltefosine, misonidazole, mitobronitol, mitoguazone dihydrochioride, mitolactol, mitomycin, mitotane, mitozanetrone hydrochloride, mizoribine, mopidamol, muitlaichilpeptide, muromonab-cd3, mustine hydrochloride, mycophenolic acid, mycophenolate mofetil, nedaplatin, nilutamide, nimustine hydrochloride, oxaliplatin, paclitaxel, pcnu, penostatin, peplomycin sulphate, pipobroman, pirarubicin, piritrexim isethionate, piroxantrone hydrochloride, plicamycin, porfimer sodium, prednimustine, procarbazine hydrochloride, raltitrexed, ranimustine, razoxane, rogletimide, roquinimex, sebriplatin, semustine, sirolimus, sizofiran, sobuzoxane, sodium bromebrate, sparfosic acid, sparfosate sodium, sreptozocin, sulofenur, tacrolimus, tamoxifen, tegafur, teloxantrone hydrochloride, temozolomide, teniposide, testolactone, tetrasodium mesotetraphenylporphine-sulphonate, thioguanine, thioinosine, thiotepa, topotecan, toremifene, treosulfan, trimetrexate, trofosfamide, tumor necrosis factor, ubenimex, uramustine, vinblastine sulphate, vincristine sulphate, vindesine sulphate, vinorelbine tartrate, vorozole, zinostatin, zolimomab aritox, zorubicin hydrochloride, an inhibitor of protein kinase A (PKA) or PKC or TrkA, an inhibitor of cAMP signaling, a nonsteroidal anti-inflammatory drug, a prostaglandin synthesis inhibitor, a local anesthetic, an anticonvulsant, an antidepressant, an opioid receptor agonist, and a neuroleptic, a benzodiazepine, a barbiturate, a neurosteroid and a inhalation anesthetic, a anesthetic and another pain killer and the like, either individually or in any combination.

All publications and patent applications herein are incorporated by reference to the same extent as if each individual publication or patent application was specifically and individually indicated to be incorporated by reference. The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A crystalline polymorph Form 2 of compound 10

Compound 10 having an x-ray powder diffraction pattern comprising peaks with degrees two-theta positions of about 5.1±0.3, 12.7±0.4, and 22.0±0.3.

2. The crystalline polymorph of claim 1, further comprising peaks with degrees two-theta positions of about 16.3±0.3 and 15.5±0.3.

3. The crystalline polymorph of claim 1, further comprising peaks with degrees two-theta positions of about 18.5±0.3 and 19.6±0.3.

4. The crystalline polymorph of claim 1, comprising five or more peaks with degrees two-theta positions selected from the group consisting of about 5.181, 9.338, 10.301, 11.616, 12.883, 15.580, 16.339, 17.321, 18.560, 18.998, 19.702, 22.042, 23.339, 23.740, 24.00, 25.441, 28.460, 29.219, 29.563, and 31.379, wherein each peak of degree two-theta has a margin of error of ±0.3.

5. The crystalline polymorph of claim 1, comprising seven or more peaks with degrees two-theta positions selected from the group consisting of about 5.181, 9.338, 10.301, 11.616, 12.883, 15.580, 16.339, 17.321, 18.560, 18.998, 19.702, 22.042, 23.339, 23.740, 24.00, 25.441, 28.460, 29.219, 29.563, and 31.379, wherein each peak of degree two-theta has a margin of error of ±0.3.

6. The crystalline polymorph of claim 1, comprising ten or more peaks with degrees two-theta positions selected from the group consisting of about 5.181, 9.338, 10.301, 11.616, 12.883, 15.580, 16.339, 17.321, 18.560, 18.998, 19.702, 22.042, 23.339, 23.740, 24.00, 25.441, 28.460, 29.219, 29.563, and 31.379, wherein each peak of degree two-theta has a margin of error of ±0.3.

7. The crystalline polymorph of claim 1, comprising peaks with degrees two-theta positions of about 5.181, 9.338, 10.301, 11.616, 12.883, 15.580, 16.339, 17.321, 18.560, 18.998, 19.702, 22.042, 23.339, 23.740, 24.00, 25.441, 28.460, 29.219, 29.563, and 31.379, wherein each peak of degree two-theta has a margin of error of ±0.3.

8. The crystalline polymorph of claim 1, having an x-ray powder diffraction pattern that is substantially similar to that of FIG. 4.

9. The crystalline polymorph of claim 1, having a differential scanning calorimetry thermogram exhibiting an endotherm with an onset of about 160° C.

10. The crystalline polymorph of claim 1, having a differential scanning calorimetry thermogram exhibiting an endotherm with a peak of about 163° C.

11. The crystalline polymorph claim 1, having a differential scanning calorimetry thermogram that is substantially similar to that of FIG. 5.

12. The crystalline polymorph of claim 1, having Infrared spectrum substantially similar to that of FIG. 17.

13. A crystalline polymorph Form 1 of compound 10

Compound 10

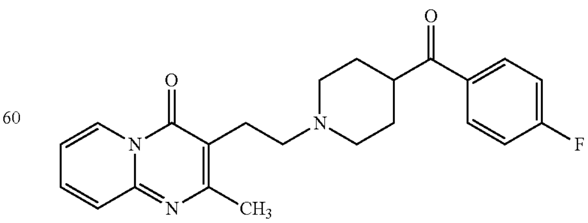

having an x-ray powder diffraction pattern comprising four or more peaks with degrees two-theta positions selected from the group consisting of about 4.482, 9.000, 12.248, 13.542, 14.596, 16.137, 17.126, 17.6667, 18.396, 19.419, 20.092, 21.885, 22.551, 23.3092, 26.787, and 27.361, wherein each peak of degree two-theta has a margin of error of ±0.3.

14. The crystalline polymorph of claim 13 comprising ten or more peaks with degrees two-theta positions selected from the group consisting of about 4.482, 9.000, 12.248, 13.542, 14.596, 16.137, 17.126, 17.6667, 18.396, 19.419, 20.092, 21.885, 22.551, 23.3092, 26.787, and 27.361, wherein each peak of degree two-theta has a margin of error of ±0.3.

15. The crystalline polymorph of claim 13 comprising peaks with degrees two-theta positions of about 4.482, 9.000, 12.248, 13.542, 14.596, 16.137, 17.126, 17.6667, 18.396, 19.419, 20.092, 21.885, 22.551, 23.3092, 26.787, and 27.361, wherein each peak of degree two-theta has a margin of error of ±0.3.

16. A crystalline polymorph Form 3 of compound 10:

Compound 10

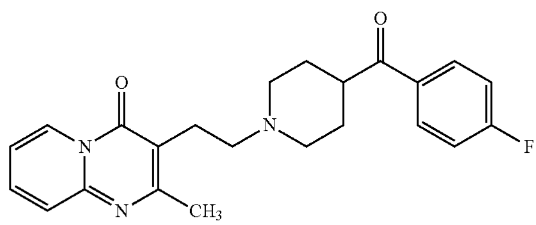

having an x-ray powder diffraction pattern comprising five or more peaks at degrees two-theta positions selected from the group consisting of about 11.070, 13.178, 14.801, 16.045, 20.301, 20.800, 21.687, 22.368, 23.048, 23.884, 24.835, 26.660, and 35.667, wherein each peak of degree two-theta has a margin of error of ±0.3.

17. The crystalline polymorph of claim 16 comprising ten or more peaks at degrees two-theta positions selected from the group consisting of about 11.070, 13.178, 14.801, 16.045, 20.301, 20.800, 21.687, 22.368, 23.048, 23.884, 24.835, 26.660, and 35.667, wherein each peak of degree two-theta has a margin of error of ±0.3.

18. The crystalline polymorph of claim 16 comprising peaks at degrees two-theta positions of about 11.070, 13.178, 14.801, 16.045, 20.301, 20.800, 21.687, 22.368, 23.048, 23.884, 24.835, 26.660, and 35.667, wherein each peak of degree two-theta has a margin of error of ±0.3.

19. A crystalline polymorph Form 4 of compound 10

Compound 10

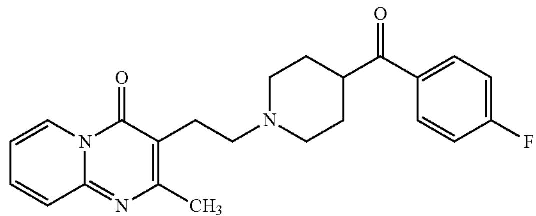

having an x-ray powder diffraction pattern comprising five or more peaks with degrees two-theta positions selected from the group consisting of about 10.473, 13.598, 14.502, 15.679, 18.338, 18.955, 19.401, 21.423, 21.861, 22.138, 23.851, 24.511, 25.815, 26.244, 27.043, 27.584, 27.948, 28.547, 29.553, and 31.200, wherein each peak of degree two-theta has a margin of error of ±0.3.

20. The crystalline polymorph of claim 19, comprising ten or more peaks with degrees two-theta positions selected from the group consisting of about 10.473, 13.598, 14.502, 15.679, 18.338, 18.955, 19.401, 21.423, 21.861, 22.138, 23.851, 24.511, 25.815, 26.244, 27.043, 27.584, 27.948, 28.547, 29.553, and 31.200, wherein each peak of degree two-theta has a margin of error of ±0.3.

21. The crystalline polymorph of claim 19 peaks with degrees two-theta positions of about 10.473, 13.598, 14.502, 15.679, 18.338, 18.955, 19.401, 21.423, 21.861, 22.138, 23.851, 24.511, 25.815, 26.244, 27.043, 27.584, 27.948, 28.547, 29.553, and 31.200, wherein each peak of degree two-theta has a margin of error of ±0.3.

22. A crystalline polymorph Form 5 of compound 10

Compound 10 having an x-ray powder diffraction pattern comprising six or more peaks with degrees two-theta positions selected from the group consisting of about 5.157, 7.600, 9.823, 10.412, 11.221, 13.456, 14.512, 15.314, 15.739, 16.325, 16.832, 17.354, 17.828, 18.485, 19.367, 20.320, 21.077, 21.708, 22.328, 23.319, 23.905, 25.197, 25.916, 27.770, 28.511, 29.132, 30.399, and 37.203, wherein each peak of degree two-theta has a margin of error of ±0.3.

23. A crystalline polymorph of claim 22 comprising ten or more peaks with degrees two-theta positions selected from the group consisting of about 5.157, 7.600, 9.823, 10.412, 11.221, 13.456, 14.512, 15.314, 15.739, 16.325, 16.832, 17.354, 17.828, 18.485, 19.367, 20.320, 21.077, 21.708, 22.328, 23.319, 23.905, 25.197, 25.916, 27.770, 28.511, 29.132, 30.399, and 37.203, wherein each peak of degree two-theta has a margin of error of ±0.3.

24. A crystalline polymorph of claim 22 comprising peaks with degrees two-theta positions of about 5.157, 7.600, 9.823, 10.412, 11.221, 13.456, 14.512, 15.314, 15.739, 16.325, 16.832, 17.354, 17.828, 18.485, 19.367, 20.320, 21.077, 21.708, 22.328, 23.319, 23.905, 25.197, 25.916, 27.770, 28.511, 29.132, 30.399, and 37.203, wherein each peak of degree two-theta has a margin of error of ±0.3.

25. A crystalline polymorph Form 2' of compound 10

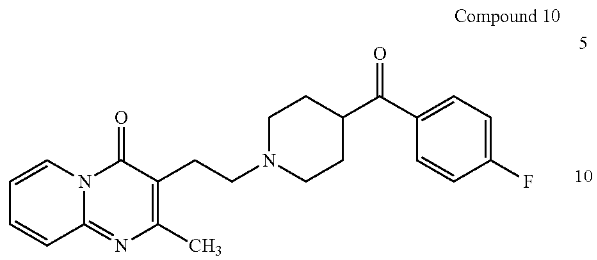

having an x-ray powder diffraction pattern comprising peaks with degree two-theta positions of about 8.8±0.3, 19.5±0.3, 23.8±0.3, and 30.8±0.3.

26. The crystalline polymorph of claim 25 comprising four or more peaks with degree two-theta positions selected from the group consisting of about 8.8±0.3, 12.5±0.3, 12.8±0.3, 16.2±0.3, 18.4±0.3, 18.8±0.3, 19.5±0.3, 22.0±0.3, 23.2±0.3, 23.8±0.3, 25.4±0.3, 29.6±0.3 and 30.8±0.3.

27. The crystalline polymorph of claim 25 peaks with degree two-theta positions selected from the group consisting of about 8.8±0.3, 12.5±0.3, 12.8±0.3, 16.2±0.3, 18.4±0.3, 18.8±0.3, 19.5±0.3, 22.0±0.3, 23.2±0.3, 23.8±0.3, 25.4±0.3, 29.6±0.3 and 30.8±0.3.

28. A crystalline polymorph Form 6 of compound 10

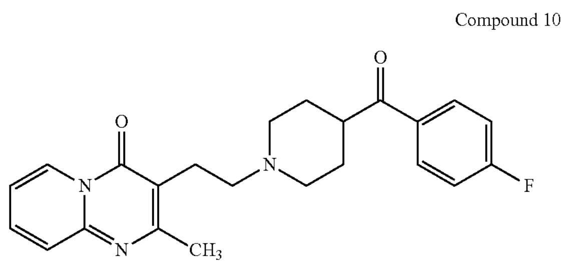 [SMILES: Cc1nc2ccccn2c(=O)c1CCN1CCC(C(=O)c2ccc(F)cc2)CC1]

having an x-ray powder diffraction pattern comprising five or more peaks with degrees two-theta positions selected from the group consisting of about 4.943, 10.108, 12.473, 12.736, 15.294, 16.131, 18.259, 18.811, 19.450, 20.500, 21.778, 23.104, 23.739, 25.279, 29.016, and 29.487, wherein each peak of degree two-theta has a margin of error of ±0.3.

29. The crystalline polymorph of claim 28 comprising ten or more peaks with degrees two-theta positions selected from the group consisting of about 4.943, 10.108, 12.473, 12.736, 15.294, 16.131, 18.259, 18.811, 19.450, 20.500, 21.778, 23.104, 23.739, 25.279, 29.016, and 29.487, wherein each peak of degree two-theta has a margin of error of ±0.3.

30. The crystalline polymorph of claim 28 comprising peaks with degrees two-theta positions of about 4.943, 10.108, 12.473, 12.736, 15.294, 16.131, 18.259, 18.811, 19.450, 20.500, 21.778, 23.104, 23.739, 25.279, 29.016, and 29.487, wherein each peak of degree two-theta has a margin of error of ±0.3.

31. The crystalline polymorph of claim 28, having an x-ray powder diffraction pattern that is substantially similar to that of FIG. 18.

32. The crystalline polymorph of claim 28, having a differential scanning calorimetry thermogram exhibiting an endotherm with an onset of about 160° C.

33. The crystalline polymorph of claim 28, having a differential scanning calorimetry thermogram exhibiting an endotherm with a peak of about 163° C.

34. The crystalline polymorph of claim 28, having a differential scanning calorimetry thermogram that is substantially similar to that of FIG. 5.

35. A crystalline polymorph Form 7 of compound 10

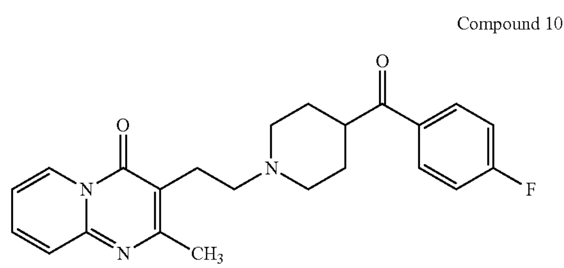 [SMILES: Cc1nc2ccccn2c(=O)c1CCN1CCC(C(=O)c2ccc(F)cc2)CC1]

or a pharmaceutically acceptable salt thereof, having an x-ray powder diffraction pattern comprising six or more peaks with degrees two-theta positions selected from the group consisting of about 5.355, 9.441, 12.880, 15.678, 16.421, 17.441, 17.990, 18.659, 19.100, 19.781, 22.081, 23.401, 23.982, 25.580, 28.461, 19.321, 29.857, 31.101, 31.438, 33.401, and 36.280, wherein each peak of degree two-theta has a margin of error of ±0.3.

36. The crystalline polymorph of claim 35 comprising ten or more peaks with degrees two-theta positions selected from the group consisting of about 5.355, 9.441, 12.880, 15.678, 16.421, 17.441, 17.990, 18.659, 19.100, 19.781, 22.081, 23.401, 23.982, 25.580, 28.461, 19.321, 29.857, 31.101, 31.438, 33.401, and 36.280, wherein each peak of degree two-theta has a margin of error of ±0.3.

37. The crystalline polymorph of claim 35 comprising peaks with degrees two-theta positions of about 5.355, 9.441, 12.880, 15.678, 16.421, 17.441, 17.990, 18.659, 19.100, 19.781, 22.081, 23.401, 23.982, 25.580, 28.461, 19.321, 29.857, 31.101, 31.438, 33.401, and 36.280, wherein each peak of degree two-theta has a margin of error of ±0.3.

38. The crystalline polymorph of claim 35, having an x-ray powder diffraction pattern that is substantially similar to that of FIG. 19.

39. The crystalline polymorph of claim 35, having a differential scanning calorimetry thermogram exhibiting an endotherm with an onset of about 160° C.

40. The crystalline polymorph of claim 35, having a differential scanning calorimetry thermogram exhibiting an endotherm with a peak of about 163° C.

41. The crystalline polymorph of claim 35, having a differential scanning calorimetry thermogram that is substantially similar to that of FIG. 5.

42. A combination of a crystalline polymorph of claim 1 with one or more pharmaceutically acceptable excipients.

43. A solid or semi-solid pharmaceutical dosage form comprising a crystalline polymorph of claim 1 and a pharmaceutically acceptable excipient.

44. A method for treating a disease, disorder, or condition associated with T-type calcium ion channels, comprising: administering a pharmaceutical composition comprising a crystalline polymorph of claim 1 to a patient in need thereof.

45. The method of claim 44, wherein the disease, disorder, or condition associated with T-type calcium ion channels is one or more of: acute pain, chronic pain, neuropathic pain, inflammatory pain, radicular pain, sciatica, back pain, head pain, neck pain, severe or intractable pain, post-surgical pain, visceral pain, cancer pain, osteoarthritis pain, nociceptive pain, breakthrough pain, or migraine.

46. The method of claim 44, wherein one or more additional active or therapeutic agents is administered to said patient in combination with the pharmaceutical composition comprising a crystalline polymorph of claim 1.

47. The crystalline polymorph of claim 35, wherein said polymorph is a salt form.

48. The method of claim 44, wherein the disease, disorder, or condition associated with T-type calcium ion channels is pain.

* * * * *